United States Patent [19]

Hagiwara et al.

[11] Patent Number: 4,959,268

[45] Date of Patent: Sep. 25, 1990

[54] POLYMER CONTAINING AMORPHOUS ALUMINOSILICATE PARTICLES AND PROCESS FOR PRODUCING THE SAME

[75] Inventors: Zenji Hagiwara, Shiga; Satoshi Ando, Osaka; Kunio Ichihashi, Osaka; Akira Dono, Osaka, all of Japan

[73] Assignees: Zenji Hagiwara, Saiga; Kanebo Ltd., Tokyo, both of Japan

[21] Appl. No.: 73,448

[22] Filed: Jul. 14, 1987

[30] Foreign Application Priority Data

Jul. 16, 1986 [JP] Japan .................................. 61-167284

[51] Int. Cl.$^5$ .......................... B32B 5/16; B05D 7/00; C01B 33/34
[52] U.S. Cl. .................................... 428/403; 428/328; 423/112; 423/118; 423/328; 423/330; 427/212
[58] Field of Search ................ 428/403, 328; 427/212; 423/118, 328, 330, 24, 112, 329; 424/132, 140, 145, 157, DIG. 7; 604/360, 367

[56] References Cited

U.S. PATENT DOCUMENTS

| | | | |
|---|---|---|---|
| 2,040,811 | 5/1936 | Nikitin et al. | 424/635 |
| 2,066,271 | 12/1936 | Irwin | 210/764 |
| 2,512,053 | 6/1950 | Calmon | 423/330 |
| 2,882,243 | 4/1959 | Milton | 423/329 |
| 2,882,244 | 4/1959 | Milton | 423/331 |
| 3,382,039 | 5/1968 | Calmon | 423/118 |
| 3,406,123 | 10/1968 | Sensol | 423/328 |
| 3,514,270 | 5/1970 | Tomita | 423/329 |
| 3,649,176 | 3/1972 | Rosback | 423/328 |
| 3,649,177 | 3/1972 | Rosback | 423/328 |
| 4,115,130 | 9/1979 | Crump et al. | 106/15 R |
| 4,264,319 | 4/1981 | Plapper et al. | 8/94.26 |
| 4,284,580 | 8/1981 | Logan et al. | 260/428.5 |
| 4,323,475 | 4/1982 | Ball et al. | 252/373 |
| 4,340,573 | 7/1982 | Vaughn et al. | 423/328 |
| 4,525,410 | 6/1985 | Hagiwara et al. | 428/198 |

FOREIGN PATENT DOCUMENTS

| | | |
|---|---|---|
| 116865 | 1/1984 | European Pat. Off. . |
| 1068232 | 11/1959 | Fed. Rep. of Germany . |
| 2352265 | 4/1975 | Fed. Rep. of Germany . |
| 576971 | 4/1946 | United Kingdom . |

OTHER PUBLICATIONS

Gellens et al., "On the Nature of the Charged Silver Clusters in Zeolites of Type A, X, and Y", Zeolites, 1981, vol. 1, pp. 11–18.

Primary Examiner—George F. Lesmes
Assistant Examiner—Christopher Brown
Attorney, Agent, or Firm—Browdy and Neimark

[57] ABSTRACT

A polymer which contains amorphous aluminosilicate particles holding metal ions having a bactericidal action is physically stable and enables an ideal antibacterial or bactericidal action by the antibacterial metal ion in an excited state. The polymer is produced by mixing an organic polymer with said amorphous aluminosilicate solid particles before the polymer is molded. Alternatively, the polymer is produced by molding an organic polymer containing amorphous aluminosilicate solid particles, and treating the molded organic polymer with a solution of a water-soluble salt of a metal having a bactericidal action, thereby allowing the metal ions to be held on at least some of the amorphous aluminosilicate solid particles.

8 Claims, 5 Drawing Sheets

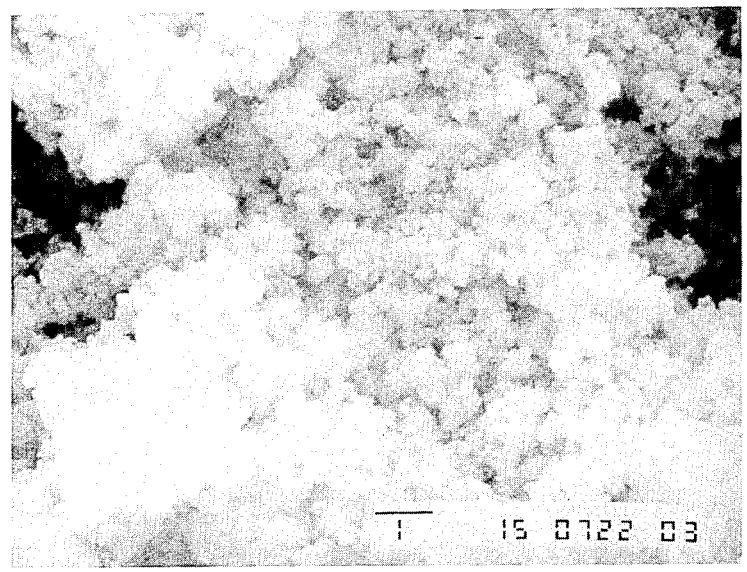
Fig. 10
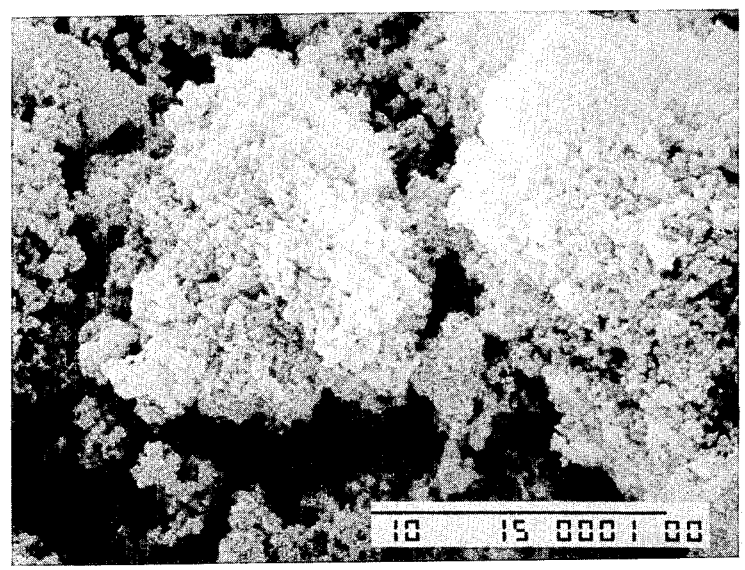

POLYMER CONTAINING AMORPHOUS ALUMINOSILICATE PARTICLES AND PROCESS FOR PRODUCING THE SAME

BACKGROUND OF THE INVENTION

1. Field of the Invention

The present invention relates to an amorphous aluminosilicate (hereinafter referred to as "AMAS") particle-containing polymer comprising AMAS solid particles having a bactericidal action and an organic polymer. The present invention also pertains to a process for producing said AMAS particle-containing polymer.

2. Description of the Related Art

It is well known for long that silver, copper and zinc ions have an antibacterial action. For example, silver ions have heretofore been widely used as a disinfectant in the form of an aqueous solution such as silver nitrate. However, silver in the form of a solution is inconvenient to handle and, therefore, the range of use of silver as a disinfectant is disadvantageously limited. Accordingly, if the above-described metal ions are held on polymers, it is possible to reduce the number of described disadvantages and expect the metal ions to be used in a wide range of fields. There have heretofore been proposed various methods of allowing polymers to hold metal ions. For example, a method in which filaments or powder of a metal is bonded or added to a polymer and a method in which a polymer is allowed to contain a metallic compound are well known. However, the former method that utilizes a metal itself suffers from the following disadvantages. Since the specific gravity and Young's modulus of a metal are considerably higher than those of an ordinary polymer, the compatibility of the metal with the polymer is inferior. Further, since a relatively large amount of metal is needed, the overall weight is increased and the production cost is raised. On the other hand, the latter method that utilizes a metallic compound has the problem that the metallic compound has a large effect on the polymer so that the range of use of the product is considerably limited. Even in the case where the effect of the compound on the polymer is not considerable, since the metal ions are merely contained in or attached to the polymer, a large amount of metal ions fall from the polymer during use. Thus, such conventional practice is unsatisfactory from the viewpoint of the lasting quality of the bactericidal power and effects. In order to improve the above-described disadvantages, there has been proposed a method wherein a polymer is allowed to contain an organofunctional group having ion exchange capacity or complexing capacity and this organofunctional group is allowed to hold metal ions. However, in this method also, the interaction between the organofunctional group and the polymer is not ignorable, and in order to avoid a considerable change in the physical properties of the polymer it is necessary to employ polymers and organofunctional groups which may be selected from the extremely limited ranges, and use a limited amount of organofunctional group, irrespective of whether an organofunctional group is introduced into a polymeric chain or an organofunctional group-containing compound is added to a polymer.

In view of these circumstances, the present inventors made various efforts to overcome the disadvantages of the prior art and, as a result, the inventors have found that a polymer which contains AMAS (amorphous aluminosilicate) particles holding antibacterial metal ions at ion exchange sites on and with particles of amorphous aluminosilicates is physically stable and has high heat resistance and this polymer enables an ideal antibacterial or bactericidal action by the antibacterial metal ions in an excited state. Thus, the above-described polymer is expected to be effectively and widely utilized. The present invention has been accomplished on the basis of this finding.

SUMMARY OF THE INVENTION

Accordingly, it is an object of the present invention to provide a polymer containing particles having a bactericidal action and a process for producing the same. More particularly, the present invention aims at providing a polymer which contains particles holding metal ions having a bactericidal action and which has less change in the physical properties and is applicable to a wide range of polymeric materials, together with a process for producing said polymer.

More specifically, the present invention is directed to an amorphous aluminosilicate particle-containing polymer which comprises amorphous aluminosilicate solid particles and an organic polymer, at least some of the amorphous aluminosilicate solid particles stably holding metal ions having a bactericidal action on ion-exchangeable sites on and within the particles. The present invention also provides a process for producing said polymer.

According to one aspect of the present invention, there is provided a process for producing a polymer containing amorphous aluminosilicate particles comprising mixing an organic polymer with amorphous aluminosilicate solid particles holding metal ions having a bactericidal action in any step before the organic polymer is molded.

According to another aspect of the present invention, there is provided a process for producing a polymer containing amorphous aluminosilicate particles comprising the steps of molding an organic polymer containing amorphous aluminosilicate solid particles, and treating the molded organic polymer with a solution of a water-soluble salt of a metal having a bactericidal action, thereby allowing at least some of the amorphous aluminosilicate solid particles to hold the bactericidal metal ions.

The above and other objects, features and advantages of the present invention will become apparent from the following description taken in conjunction with the accompanying drawings.

BRIEF DESCRIPTION OF THE DRAWINGS

FIGS. 1 to 5 respectively show X-ray diffraction patterns of various AMAS powders having an antibacterial action, in which:

FIG. 1 shows X-ray diffraction patterns of Ag-AMAS obtained in Production Example 4-A;

FIG. 2 shows X-ray diffraction patterns of Ag-AMAS obtained in Production Example 4-C;

FIG. 3 shows X-ray diffraction patterns of Cu-AMAS obtained in Production Example 5-A;

FIG. 4 shows an X-ray diffraction pattern of Zn-AMAS obtained in Production Example 6-A; and FIG. 5 shows an X-ray diffraction pattern of Zn-AMAS obtained in Production Example 6-B.

In FIGS. 1 to 3, the curves 1, 2, 3 and 4 show diffraction lines of AMAS powders having an antibacterial action processed at 100° C., 350° C., 450° C. and 550° C., respectively; and FIGS. 4 and 5 show the results of diffraction carried out an AMAS powders dried at 100° C.

FIG. 6 shows an electron microscopic photograph of Cu-AMAS obtained in Production Example 5-A, in which the length of the reversed white portion in 1 μm;

FIG. 10 shows an electric microscopic photograph of a non-antibacterial amorphous aluminosilicate, in which the length of the reversed white portion is 1 μm.

DETAILED DESCRIPTION OF THE INVENTION

Figure 1:
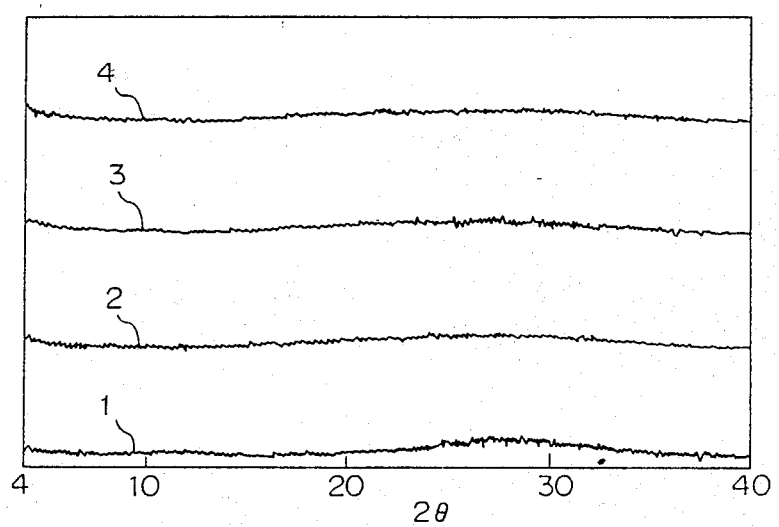
Figure 2:
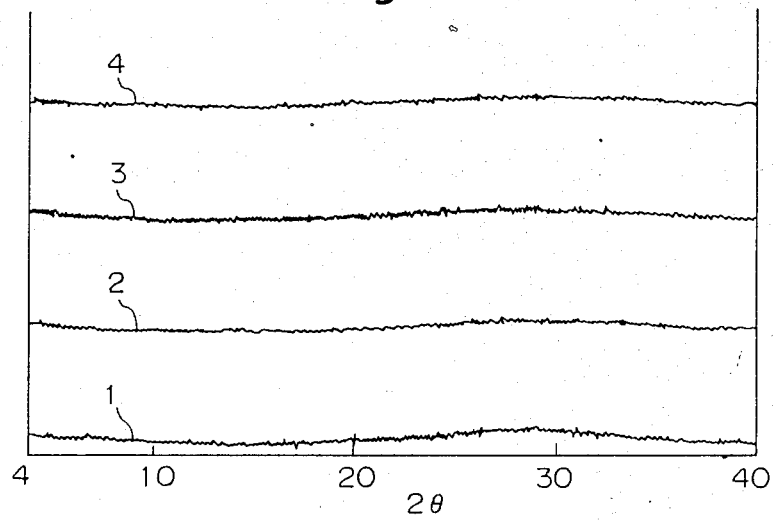
Figure 3:
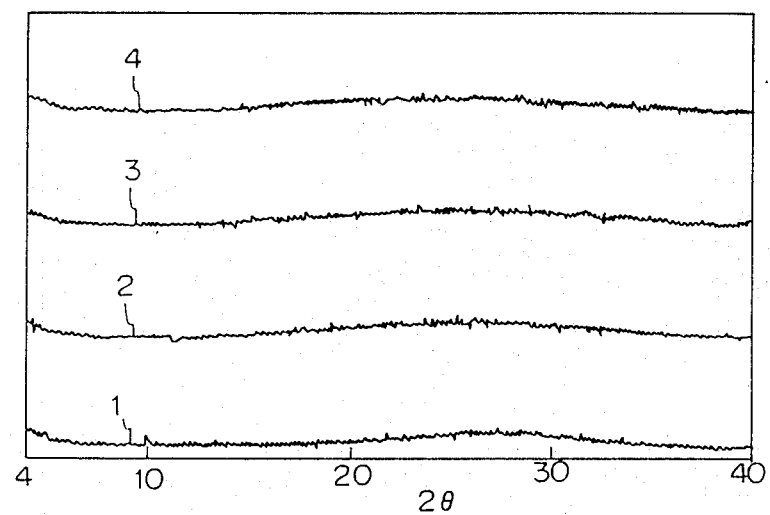
Figure 4:
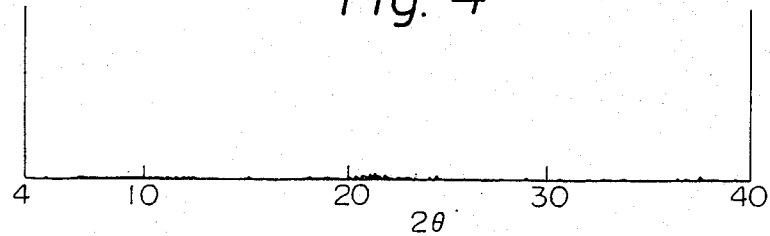
Figure 5:
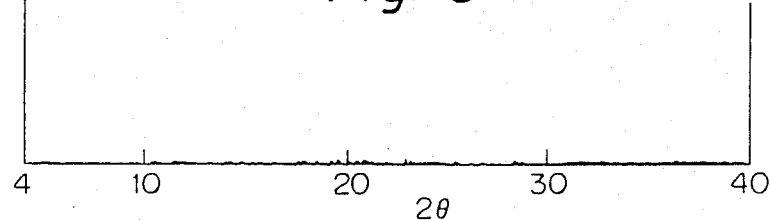

Amorphous aluminosilicate solid particles having a bactericidal action which can be employed in the present invention include natural and synthetic amorphous aluminosilicates having at least one kind of bactericidal metal ion held stably on the ion-exchangeable portion thereof. Preferable examples of bactericidal metal ions include silver, copper, zinc, mercury, tin, lead, bismuth, cadmium and chromium ions. Accordingly, it is possible to use the above-described bactericidal metals alone or in combination for the above-described purposes.

Aluminosilicate which is employed in the present invention as a support for holding antibacterial metal ions is porous and has a three-dimensionally developed skeleton which is judged to be amorphous from both an X-ray photograph and an electron microscopic photograph. The parent body or support preferably has a specific surface area of at least 5 m²/g.

It is possible to use in the present invention an amorphous aluminosilicate (AMAS) having an antibacterial and/or bactericidal action of the formula:

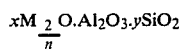

(wherein M is n (1) one element selected from among Ag, Cu, Zn, Hg, Sn, Pb, Bi, Cd and Cr (all are antibacterial or bactericidal metals), or (2) a monovalent or divalent metal or ammonium ion (NH$^{4+}$) other than those mentioned in the paragraph (1) may coexist with one of more elements selected from the antibacterial or bactericidal metal ions mentioned in the paragraph (1);

(3) a small amount of trivalent or other polyvalent metal other than those mentioned in the paragraphs (1) and (2) may present in the AMAS;

x is a number between 0.6 and 1.8 inclusive;

y is a number between 1.3 and 50 inclusive, preferably 1.3 to 30; and n is the valence of M).

It is also possible to use in the present invention a composition having an antibacterial and/or bactericidal action, which consists essentially of an amorphous aluminosilicate of the formula:

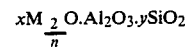

(wherein M is one element selected from among silver, copper, zinc, mercury, tin, lead, bismuth, cadmium and chromium; n is the valence of M; x is a number preferably ranging from 0.6 to 1.8 inclusive; and y is a number between 1.3 and 50 inclusive, preferably 1.3 to 30), and an amorphous aluminosilicate of the formula:

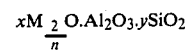

[wherein a part of M is a monovalent or divalent metal having ion exchangeability such as sodium, potassium, lithium, iron (II), magnesium (II), calcium (II), cobalt (II) or nickel (II) or ammonium ion (NH$^{4+}$) (it should be noted that M partially contains at least one metal having an antibacterial or bactericidal action selected from among silver, copper, zinc, mercury, tin, lead, bismuth, cadmium and chromium); n is the valence of M; x is a number preferably ranging from 0.6 to 1.8 inclusive; and y is a number between 1.3 and 50 inclusive, preferably 1.3 to 30]. It is a matter of course that the above-described AMAS (amorphous aluminosilicate) may contain a small amount of a trivalent or other polyvalent metal.

Since M in the above-described formulae has cation exchange capacity, a necessary amount of an antibacterial metal used in the present invention can readily and stably held on the AMAS which serves as a support or a parent body by employing the ion exchange method. Although there is no particular restriction on the cation exchange capacity of AMAS used in the present invention, a preferably value therefore is at least 1 meq/g (on an anhydrous basis) from the viewpoint of the amount of bactericidal metal ions to be held.

The specific surface area of AMAS particles used in the present invention is at least 5 m²/g (on an anhydrous basis), and the molar ratio of SiO$_2$/Al$_2$O$_3$ which are components of AMAS is at least 1.3, preferably, between 1.3 and 30 inclusive.

A solution of a water-soluble salt of any one of the above-specified bactericidal metals used in the present invention, e.g., silver, copper or zinc, readily exchanges ions with AMAS specified in the present invention. Therefore, by utilizing such a phenomenon, at least one kind of necessary metal ions selected from the aforementioned group can be combined with the exchange group in the solid phase of AMAS and thereby held thereon stably. However, it is necessary in order to stably hold the metal ions to satisfy the two conditions that the molar ratio of SiO$_2$/Al$_2$O$_3$ in AMAS stably holding the metal ions must be at least 1.3 and the specific surface area must be at least 5 m²/g. It has been confirmed that, if these conditions are not satisfied, it is impossible to obtain a porous object which has acid resistance, heat resistance and an effective bactericidal action. The reason for this is considered to be shortage of the absolute amount of metal ions fixed to AMAS in a stage wherein they can exhibit the bactericidal effect. In other words, it may be attributable to physicochemical properties such as the capacity of the exchange group of AMAS, and the reaction rate and accessibility of exchangeable ions.

It has been confirmed that AMAS in which the $SiO_2/Al_2O_3$ molar ratio is above the lower-limit value in the aforementioned range is capable of uniformly holding metal ions having a bactericidal action and bactericidal ions which are present at active points on the supporting parent body exhibit satisfactory bactericidal effect. On the other hand, AMAS which has a $SiO_2/Al_2O_3$ molar ratio of below 1.3 and consequently has a relatively low silica proportion suffers from the disadvantage that the alkali resistance lowers as the $SiO_2$ content decreases. Accordingly, employment of such a raw material undesirably limits the range of use of antibacterial AMAS. Natural or synthetic AMAS having the aforementioned $SiO_2/Al_2O_3$ molar ratio is satisfactorily usable in the antibacterial or bactericidal fields which are commonly considered to be applicable fields of the present invention from the viewpoint of acid, alkali and heat resistances. From the economic point of view also, AMAS's specified in the present invention can be prepared at low costs and it is therefore advisable to use them. For this reason also, the $SiO_2/Al_2O_3$ molar ratio must be 1.3 or more.

The amorphous aluminosilicate according to the present invention can be derived from $xNa_2O\cdot Al_2O_3\cdot ySiO_2$ in the following manner.

An alkali solution (Solution-C) the alkalinity of which is within a range of 1.2 to 3.5N is maintained under stirring. Into Solution-C are separately added a predetermined amount of a sodium aluminate solution (Solution-A) containing free alkali and a predetermined amount of a sodium silicate solution or a colloidal silica solution (Solution-B) containing free alkali, so as to prepare a slurry which contains an amorphous aluminosilicate (principal component: $Na_2O\text{-}Al_2O_3\text{-}SiO_2$) constituted by finely divided particles which are only slightly soluble in water. Then, the slurry is aged to produce an amorphous aluminosilicate. In this method, the addition of Solution-A and Solution-B into Solution-C is carried out so that the Si/Al ratio in the resultant mixture may be kept within a range of 0.7 to 27.6 during and after the addition, and the mixing is effected at 55° C. or lower. In addition, Solution-A and Solution-B are prepared so that both the alkalinity of the aqueous solution phase during the formation of the slurry and that during the aging are kept within ±0.30N of the alkalinity of Solution-C prepared in advance, in order to suppress any fluctuation of the alkalinity throughout the whole process, thereby producing an aluminosilicate of the formula:

$$xNa_2O\cdot Al_2O_3\cdot ySiO_2$$

(wherein x and y are the same as those defined above).

The other compounds having an ion exchange metal can be derived by ion exchange of the above-described sodium-substituted compound.

In ordinary synthesis of AMAS (amorphous aluminosilicate), it is extremely easy to prepare AMAS which is constituted by porous particles having a specific surface are (SSA) of at least 5 m²/g and an average particle diameter (Dav) of 6 μm. The above-described M has ion exchangeability, and M is allowed to exchange a necessary amount of at least one of the antibacterial or bactericidal metal ions described below so that the metal ions are stably held on AMAS of 5 m²/g (SSA) which serves as a parent body or solid phase, whereby it is possible to obtain an active AMAS composition having antibacterial and bactericidal actions according to the present invention.

AMAS which is employed in the present invention is preferably in the form of a powder or a granular shape, and the particle diameter thereof may be appropriately selected in accordance with the use. When AMAS is used to form a relatively thick molded product, for example, when it is applied to various kinds of container, pipes, granular materials or fibers having a relatively high denier, the particle diameter may be selected so as to fall within the range from several microns to several tens of microns or may be above several hundreds of microns, whereas, when AMAS is used to form fibers having a relatively low denier or films, the particle diameter is preferably set so as to be relatively small. For example, in the case of fibers for garments, the particle diameter is preferably selected so as to be 7 microns or less, particularly preferably 2 microns or less. In the case of films or nets, the adequate average particle diameter is about 3 to 8 microns. When AMAS is added to a polymer, it is generally preferable to set the average particle diameter (Dav) so as to be 20 μm or less.

When the above-described powdered or granulated AMAS is to be incorporated into an organic polymer, it is necessary to remove water content from AMAS to an extent that is determined by particular requirements by heating AMAS under a vacuum or normal pressure in advance. The degree to which water content is to be removed depends on the kind and properties of the polymer employed. Dispersion of AMAS in the polymer is generally carried out under heating using a various kinds of kneading machine; in this case, the polymer may, of course, contain a third component, that is, the polymer may contain, for example, a various kinds of plasticizer, organic or inorganic additive, filler, compounding agent, lubricant, ultraviolet absorbing agent, stabilizer, oxidation inhibitor, reinforcing agent, coloring agent and delustering agent. Further, the polymer may contain a foaming agent, fire retardant additive, modifier, pigment, etc. The polymer containing AMAS according to the present invention may be processed to various kinds of molded product by means of a variety of molding processes such as injection molding, compression molding, laminate molding, extrusion, inflation, T-die extrusion, blow molding, etc.

There is no particular restriction on organic polymers which can be employed in the present invention, and it is possible to use synthetic or semisynthetic organic polymers, for example, thermoplastic synthetic polymers such polyethylene, polypropylene, polystyrene, polyvinyl chloride, polyvinylidene chloride, polyamide, polyester, polyvinyl alcohol, polycarbonate, polyacetal, ABS resin, acrylic resin, fluorine resin, polyurethane elastomer and polyester elastomer, thermosetting synthetic polymers such as phenolic resin, urea resin, melamine resin, unsaturated polyester resin, epoxy resin and urethane resin, and regenerated or semisynthetic polymers such as rayon, cuprammonium resin, acetate and triacetate. When a high bactericidal or antibacterial effect is needed, the molded product preferably has a large surface area. Shaping the molded product in the form of fibers may be one of the methods of increasing the surface area of the molded product. From this point of view, preferable organic polymers are fiber-forming polymers, for example, synthetic polymers such as nylon 6, nylon 66, polyvinyl alcohol, polyvinyl chloride, polyvinylidene chloride, polyethylene terephthalate, polybutylene terephthalate, polyacrylonitrile, polyethylene, polypropylene and copolymers thereof, and regenerated or semisynthetic polymers such as rayon, cuprammonium resin, acetate and triacetate. Another method of increasing the surface area of the molded product may be formation of a polymeric foam. From the viewpoint of trial production of such foams, examples of preferable organic polymers are polyethylene, polystyrene, polypropylene, ethylene-vinyl acetate copolymer (EVA), polyvinyl chloride, acrylonitrile-butadiene-styrene resin (ABS), acrylic resin, polyurethane, urea resin, epoxy resin, phenolic resin, nylon, polyvinyl alcohol, viscose and rubber. These foaming materials may contain a plasticizer, stabilizer, filler, oxidation inhibitor, lubricant, coloring agent, modifier, etc.

The AMAS particle-containing polymer according to the present invention comprises AMAS solid particles and an organic polymer such as those described above, wherein at least some of the AMAS solid particles are holding at least one kind of metal ions having a bactericidal action. The proportion of the AMAS solid particles with respect to the whole is usually from 0.005 to 50% by weight (on an anhydrous AMAS basis) although it depends on the kind and properties of the polymer employed. An AMAS content less than the above-described lower-limit value is unsatisfactory from the viewpoint of the bactericidal or antibacterial effect and the lasting quality of this effect. An AMAS content in excess of the upper-limit value in the above-described range causes no change in the bactericidal effect, but as the AMAS content increases, the change in physical properties of the polymer increases, so that the range of use of polymeric molded products is limited undesirably. From this point of view, the AMAS solid particle content is preferably selected so as to fall within the range from 0.01 to 35% by weight. When the polymer containing AMAS particles according to the present invention is employed in the form of fibers, it is generally preferable to add AMAS particles in the range from 0.05 to 10% by weight.

The aforementioned antibacterial or bactericidal metal ions used in the present invention must be stably combined with and held on AMAS solid particles by means of ion exchange reaction. An antibacterial or bactericidal metal which is simply adsorbed or attached to AMAS solid particles without being subjected to ion exchange is unsatisfactory in the bactericidal effect and the lasting quality of this effect. The present inventors have found that there are two methods which can be employed to allow AMAS serving as a support or parent body to stably hold bactericidal metal ions. The first method comprises mixing an organic polymer with metal-AMAS having bactericidal power. The second method comprises mixing an organic polymer with AMAS particles or powder, molding the mixture into a desired one of the various shapes, and subjecting the resultant polymeric molded product to ion exchange, thereby allowing AMAS parent body within the polymer to hold bactericidal metal ions.

The first method of the present invention will first be explained. This method utilizes metal-AMAS having bactericidal power which can be prepared at ordinary temperatures or high temperatures utilizing ion exchange reaction as described above.

To convert various AMAS's (specific surface area $>5$ m$^2$/g) specified in the present invention into, for example, silver-containing silicates, a water-soluble salt solution such as silver nitrate is generally employed to convert an AMAS into Ag-AMAS. it is necessary in order to prepare Ag-AMAS of excellent quality that the concentration of this solution be set so as not to be excessively high and the pH of the solution be maintained in the neutral or slightly acidic region. If the silver ion concentration is excessively high or the pH of the solution is excessively high, e.g., 7 or more, during the conversion of AMAS into Ag-AMAS, silver ions are substituted by exchangeable ions in the solid phase of the AMAS by ion exchange and, at the same time, silver oxide or hydroxide is undesirably deposited on the solid phase of the AMAS. Accordingly, the porosity of the resultant AMAS is lowered, and even if the specific surface area is not considerably reduced, the presence of silver oxide per se deteriorates the bactericidal power. In order to prevent deposition of excessive silver on the solid phase, it is necessary to maintain the silver solution concentration at a diluted level, e.g., 0.5M AgNO$_3$, or less. The safest AgNO$_3$ concentration is 0.3M or less. It has been confirmed that, when ion exchange is carried out within the neutral or slightly acidic region using a AgNO$_3$, solution having said concentration, the specific surface area of the resultant Ag-AMAS is substantially equal to that of the AMAS as a raw material for conversion, and the bactericidal effect is exhibited under the optimal conditions and is long lasting.

When AMAS's (specific surface area $>5$ m$^2$/g) defined in the present invention are converted into Cu-AMAS, a similar phenomenon to that in the preparation of the above-described Ag-AMAS may occur depending upon the concentration of the copper salt employed for ion exchange and the pH of the solution during the ion exchange. For example, to convert an AMAS into Cu-AMAS by ion exchange reaction, if the concentration of the copper salt employed is excessively high, e.g., 1.5 to 2 M CuSO. solution, and the pH of the solution is excessively high, copper ions (Cu$^{2+}$) perform ion exchange with exchangeable ions in the solid phase and are thereby held on the solid phase and, at the same time, a basic compound, e.g., Cu$_3$(SO$_4$)(OH)$_4$, is deposited on the surface and inside of the AMAS. Accordingly, the porosity of the AMAS is lowered and the specific surface are thereof is considerably reduced, disadvantageously. In order to prevent such deposition of excessive copper on the solid phase, it is preferable to set the concentration of the employed water-soluble copper solution at a diluted level, e.g., 0.3M or less, and maintain the pH of the solution within the slightly acidic region during the ion exchange. It has been confirmed that, when ion exchange is carried out under such conditions, the specific surface are of the resultant Cu-AMAS is substantially equal to that of the raw material before the conversion and the bactericidal effect of the Cu-AMAS can be exhibited in the optimal conditions, advantageously. In conversion of an AMAS into Zn-AMAS, if the concentration of the salt employed is about 3M or less, there is substantially no fear of solid matter being deposited on the solid phase of the AMAS, although in the conversion of an AMAS into Ag- or Cu-AMAS solid matter may be deposited on the solid phase of the AMAS depending upon the concentration and pH of the salt employed in the ion exchange as described above. Zn-AMAS which may be employed in the present invention can readily be obtained by using a salt solution (slightly acidic) having a concentration of about 3M or less.

When ion exchange reaction is carried out batchwise to convert AMAS into Ag-, Cu- or Zn-AMAS, it suffices to dip AMAS as a raw material in a salt solution having the above-described concentration. In order to increase the bactericidal metal ion content in the AMAS material, it is only necessary to increase the number of times of the batch process. When a specified AMAS material is to be processed by a column method using a salt solution having the above-described concentration, the AMAS material is filled in an ion exchange adsorbing tower, and the salt solution is passed therethrough at an appropriate flow velocity, thereby enabling a target metal-AMAS to be obtained easily.

The bactericidal metal content in the above-described metal-AMAS (on an anhydrous basis) depends on the kind of the AMAS employed. In general, the silver content in the Ag-AMAS is 20% or less by weight, preferably from 0.001 to 12% by weight. In the case of copper and zinc, the copper or zinc content in the Cu- or Zn-AMAS (on an anhydrous basis) is generally 15% or less by weight, preferably from 0.01 to 10% by weight. Silver, copper and zinc ions can be employed in combination so as to be utilized for the bactericidal purposes in the form of composite AMAS particles. In this case, the total amount of metal ions may be 25% or less by weight with respect to the metal-AMAS (on an anhydrous basis), preferably from 0.001 to 15% by weight, although the preferable range depends on the composition of the employed metal ions. The content of a bactericidal metal which can be employed in the present invention other than those described above, for example, mercury, tin, lead, bismuth, cadmium or chromium, in the metal-AMAS may be determined on the basis of the amounts of the above-described bactericidal metals.

It should be noted that the bactericidal effect is not deteriorated even if antibacterial metal, e.g., silver, copper and zinc, and other metal ions, e.g., sodium, potassium, calcium or other non-antibacterial metal ions, coexist in an AMAS. Therefore, existence or coexistence of these ions has no adverse effect on the bactericidal power.

Next, a metal-AMAS is mixed with an organic polymer so that the above-described content may be reached, thereby obtaining a composition of the present invention. The amount (A wt %) of a bactericidal metal with respect to the metal-AMAS and the amount (B wt %) of the metal-AMAS with respect to the composition are related to the bactericidal effect. More specifically, if A is large, B may be reduced, whereas, if A is small, B must be increased. In order to allow the composition of the present invention to effectively exhibit its bactericidal effect, it is necessary to adjust the product of A and B to 0.01 or more for Ag-AMAS and to 0.1 or more for Cu- or Zn-AMAS. An AMAS having a bactericidal effect may be mixed with a polymer at any time and in accordance with any procedure, and there are no particular restrictions on the mixing timing and procedure. For example, AMAS may be mixed with a monomer as a raw material before polymerization; AMAS may be mixed with a reaction intermediate; AMAS may be mixed with a polymer after polymerization; AMAS may be mixed with polymer pellets before molding; and AMAS may be mixed with a molding dope, e.g., a spinning dope. These procedures will be regarded as meaning "mixing an AMAS with an organic polymer" hereinafter and in the appended claims. The point is to adopt an optimal procedure in accordance with the properties of the polymer employed and the characteristic features of each individual process. In general, it is preferable to adopt the procedure in which an AMAS is mixed with a polymer immediately before it is molded. However, there may be cases where it is preferably to mix an AMAS with a monomer in order to achieve excellent dispersion of particles. The metal-AMAS may be dried, if desired, before being mixed with a polymer as described above. Drying conditions may appropriately be selected within the range from 80° to 500° C. under ordinary or reduced pressures. The drying process is preferably carried out under a vacuum at a temperature from 100° to 350° C.

The second process according to the present invention will next be explained. The second process is basically similar to the first process although the timing at which the ion exchange is carried out is different from that in the first process. First, an AMAS defined in the foregoing which is in the form of particles or powder is mixed with a polymer without being subjected to ion exchange. In this case, the preferable range of AMAS content is the same as in the first process. There are no particular restrictions on the mixing timing and procedure. The AMAS may be mixed with the polymer in any step from the preparation of the raw material to the molding of the polymer in a manner similar to that in the first process. If it is necessary to dry the AMAS, drying may be carried out in the same way as in the first process. In accordance with the second process, the AMAS-containing polymer thus obtained is formed into a molded product, which is then subjected to an ion exchange treatment with a solution containing antibacterial metal ions. There are no particular restrictions on the kind and configuration of the molded product. For example, the molded product may be in the form of an intermediate molded product such as pellets or in the form of a final product. A porous molded product having a large specific surface area is preferable for the purpose of increasing the ion exchange efficiency. Accordingly, it is preferable to form the polymer into molded products having a relatively small diameter and thickness or air-permeable porous products, for example, granules, film, sheet, foam or fibers. The ion exchange process maybe carried out on the basis of the above-described ion exchange process for AMAS. More specifically, a polymeric molded product containing AMAS is treated at ordinary or high temperatures with a solution of a water-soluble salt of a metal having a bactericidal action. In this case, the concentration of the metal salt solution is preferably set so as to be 0.5M or less, particularly preferably 0.3M or less, in the case of $AgNO_3$, and 0.3M or less, particularly preferably 0.1M or less, in the case of $CuSO_4$. If the concentration of the above-described silver salt or copper salt aqueous solution is excessively high, a silver oxide or a basic copper compound may be deposited on the solid phase, resulting in the bactericidal effect being lowered, disadvantageously. Since such phenomenon is not found in the case of a zinc salt, the polymeric molded product may be treated with a solution having a concentration of about 2 to 3M. The treatment may be carried out either batchwise or continuously. In order to increase the amount of bactericidal metal ions held on the support, it suffices to increase, for example, the number of times of the batch process. In the case of a continuous process, it suffices to increase the processing time.

The second process of the present invention is based on the two discoveries that AMAS which is dispersedly trapped in a polymer still possesses its ion exchangeability and that it is possible to allow said AMAS to stably hold bactericidal metal ions by an appropriate ion exchange treatment. The rate at which the exchange groups of AMAS in the polymer are subjected to ion exchange is depend upon the properties and structure of each individual polymer. In the case of a porous polymer having relatively high hydrophilic nature, metal ions which are exchangeable ions permeate into the inside of the polymer by diffusion together with water, and the exchange groups of AMAS inside the polymer are also subjected to ion exchange. However, it has been confirmed that, even in the case of a hydrophobic polymer, the exchange groups of AMAS in the vicinity of the surface of the polymer are subjected to ion exchange at a considerably high rate even at ordinary temperatures and the rate becomes higher as the contact time increases or as the temperature rises. The bactericidal power of the AMAS particle-containing polymer according to the present invention mainly depends on the bactericidal AMAS incorporated therein, but the bactericidal power against the atmosphere which is in contact with the polymer is considered to be dependent on the metal ions which are present at or near the outer or inner surface of the molded product. Therefore, if the bactericidal polymeric molded product is used for the purpose of sterilization of the atmosphere which is in contact therewith only, AMAS near the surface of the molded product alone is needed to hold bactericidal metal ions, and this is efficient from the viewpoint of utilization of bactericidal metal ions. In any case, the proportion of the bactericidal metal with respect to the total amount (on an anhydrous basis) may be 20% or less by weight, preferably from 0.001 to 12% by weight, in the case of silver as described above. In the case of copper or zinc, the amount may generally be 15% or less by weight, preferably from 0.01 to 10% by weight. In the case of using silver, copper and zinc in combination, the total amount of metal ions is preferably selected so as to fall within the range from 0.001 to 15% by weight. Further, existence or coexistence of other metal ions has no adverse effected on the bactericidal power.

The AMAS content (B wt %) in a polymer containing AMAS particle and the antibacterial metal ion content (A wt %) in the metal-AMAS in which the metal ions is held by an ion exchange treatment are related to the magnitude of the bactericidal effect in the same way as that mentioned in the description of the first process. More specifically, if B is large, A may be reduced, whereas, if B is small, A must be increased. It is preferable to adjust the product of A and B to 0.01 or more in the case of silver and to 0.1 or more in the case of copper or zinc.

A polymer containing AMAS particles according to the present invention may contain a third component other than metal-AMAS as has been already described, and a liquid or an organic solvent may also be contained in the polymer as a third component other than those which have already been mentioned. When a polymer containing AMAS particles according to the present invention is used in the form of a molded product, there are no particular restriction on the configuration and size thereof. The way in which metal-AMAS particles are distributed in a molded product may appropriately be contrived, but, since the bactericidal power of an AMAS particle-containing polymer of the present invention against the atmosphere is considered to be mainly dependent upon the amount of metal ions which are present at and near the surface of the molded product, it is appropriate that a metal-AMAS in the first or second process be concentrated on or near the outer or inner surface of a molded product. For example, an AMAS according to the present invention may be contained in the outer layer of a multilayer structure. In the case of fibers, an AMAS may be contained as a component of the sheath of a yarn having a core-and-sheath cross-sectional structure by utilizing a known conjugate spinning technique.

The bond strength between AMAS defined in the present invention on the one hand and, on the other, silver, copper, zinc and other antibacterial metal ions which have already been mentioned is considerably high in contrast to that in the simple physical adsorption of an antibacterial metal or a compound thereof by an adsorptive substance such as activated charcoal or alumina. Accordingly, the strong bactericidal power of a polymer containing metal-AMAS particles and the long lasting quality thereof are specially noteworthy as characteristic advantages of the present invention. AMAS such as that specified in the present invention advantageously has high reactivity with bactericidal $Ag^+$, $Cu^{2+}$ and $Zn^{2+}$ or antibacterial metal ions such as those which have already been described. More specifically, exchangeable metal ions in AMAS are readily exchanged for $Ag^+$, $Cu^{2+}$ and $Zn^{2+}$ or other bactericidal cations which may be employed in the present invention, and such bactericidal metal ions are stably held on the AMAS serving as a parent body with high holding power. AMAS specified in the present invention has high selective adsorptivity with respect to $Ag^+$, $Cu^{2+}$ and $Zn^{2+}$ and exhibits particularly high ion exchange adsorptivity with respect to $Ag^+$. This fact shows that, even when a polymer containing AMAS particles according to the present invention is used in water or a liquid containing various kinds of metal ion for the bactericidal purposes, the used bactericidal cations are stably held in the AMAS support or parent body for a long period of time and the bactericidal power is long lasting. As described in Examples (explained later), the amount of elution of an antibacterial metal into water from a polymeric molded product containing an AMAS having antibacterial power is considerably small, i.e., from several PPb to several tens of PPb, and the amount of elution of antibacterial metal is only several tens of PPB even after three months has elapsed after the start of the use.

In addition, AMAS specified in the present invention has a considerably large exchange capacity so that it is advantageously possible to increase the amount of bactericidal $Ag^+$, $Cu^{2+}$ or $Zn^{2+}$ to be held thereon according to need. It is also advantageously possible to readily adjust by ion exchange process the amount of an antibacterial metal to be contained in the AMAS particles which are in turn contained in a polymer of the present invention in accordance with the application of the polymer.

Further, the addition of AMAS defined in the present invention to a polymer causes no change in the physical properties of the polymer nor lowering in its strength. Therefore, it is possible to select a desired one from a wide range of polymeric materials.

Since a polymer containing AMAS particles according to the present invention includes a polymeric substance as a main body, it can be formed into products having various shapes and sizes by employing the aforementioned molding processes. For example, it is possible to form the polymer into granules, sheet, film, net, fibers, various kinds of container, tape, packing and other molded articles having desired shapes, and it is therefore possible to utilize the polymer of the present invention in a considerably wide ranges of uses where bactericidal power is needed. If a polymer containing AMAS particles according to the present invention is dissolved or dispersed in a liquid to thereby impart fluidity thereto, it is possible to apply the polymer to a wide variety of materials such as antibacterial paints, coating agents, detergents, cement or organic joint fillers for tiles (e.g., acrylic emulsion) and wall materials. Further, it has been confirmed that the polymer of the present invention enables application of antibacterial or bactericidal surface coating to various kinds of coated paper and permits an antibacterial or bactericidal function (with respect to general bacteria and fungi) to be imparted to various kinds of paper in the paper-making step. In addition, a bactericidal polymer according to the present invention may contain a substance having a different function so that a composite function consisting of the above-described bactericidal function and another function may be exhibited. Examples of such functional substances include activated charcoal, silica gel, zeolite and alumina. The use of these functional substance in combination with the bactericidal polymer enables the deodorizing and absorbing effects and moisture-absorption effect to be intensified.

A molded product formed from a polymer containing AMAS particles according to the present invention can be used in the form of a mixture or composite with a polymeric molded product of the same or different kind. For example, in the case of fibers, they may be formed into an antibacterial fibrous structure widely modified in terms of hand and feel as well as function by mixed-spinning or mixed-weaving or cross-weaving or cross-knitting together with fibers containing no metal-AMAS.

Since in the present invention bactericidal metal ions are uniformly dispersed in a polymer and held on AMAS which serves as a carrier, active metal ions are dispersed in the polymer even more uniformly and widely than in the case where a metal itself is used. Thus, the bactericidal effect offered by the present invention is advantageously strong. In addition, since the bactericidal metal ions are stably held in the AMAS for a long period of time, the safety level is high and the present invention is superior from the viewpoint of the lasting quality of the bactericidal effect.

The present inventors have found that, if, in preparation of a polymer containing AMAS having a bactericidal or antibacterial action, the AMAS causes an interaction, for example, a reaction, with the polymer or a plasticizer or other additive contained therein to produce an adverse effect on the bactericidal or antibacterial power, it will be possible to effectively cope with the undesirable situation by treating the bactericidal or antibacterial AMAS in the form of particles or powder with a coating agent in advance so as to cover or wet the surface of the AMAS with a coating film, and using the AMAS which is thus inactivated to prepare a bactericidal or antibacterial polymer. In other words, it has been found that the application of coating to the AMAS holding bactericidal metal ions causes almost no lowering in the antibacterial power and antifungal effect of the AMAS and permits these effects to be long lasting. The present invention has been accomplished on the basis of this finding. For example, silicone resin coating agents or fluorine resin coating agents may preferably be employed in the present invention to coat bactericidal AMAS in the form of particles or powder. Solutions or diluted solutions of these coating agents are preferably used for surface treatment of powdered or granulated AMAS holding bactericidal metal ions specified in the present invention. Fire-retardant solvents are appropriately employed as diluents for the above-described coating agents. In the above-described treatment of bactericidal AMAS, it is preferable to dip the AMAS in a predetermined amount of coating agent or dilute solution thereof. The dipping may be carried out at ordinary or high temperatures. After the dipping, the liquid phase is separated from the solid phase, and the latter is heated to remove the solvent used for dilution from the solid phase, thus obtaining AMAS treated with a predetermined amount of coating agent. The resultant AMAS is pulverized to adjust the particle size to a desired level and is then mixed with a polymer. The above-described dipping may be replaced with a method wherein a mixture which is obtained by mixing together bactericidal AMAS and a predetermined amount of coating agent or diluted solution thereof is kneaded at ordinary or high temperatures using a kneading machine. This method makes it possible to obtain AMAS uniformly coated with the coating agent with less secondary cohesion. If the coated AMAS is further subjected to coating in the same way as the above-described dipping before being mixed with a polymer, the AMAS is uniformly dispersed in the polymer, advantageously. Preferable examples of silicone coating agents which can be employed in the present invention include dimethyl siloxane coating agents such as KF-96 (trade name; manufactured by Shin-etsu Chemical Industry Co., Ltd.), methyl hydrogen polysiloxane coating agents such as KF-99, methyltrinitrosilane coating agents such as KC-88, and silane coupling agent such as KBM-3103C. These commercially available products are relatively stable both chemically and thermally and have excellent durability and are therefore suitably employed as coating agents for AMAS specified in the present invention. More specifically, the use of these coating agents enables stable silicone coating film to be formed on the AMAS. It should be noted that, when the above-described silicone coating agents are diluted, a variety of solvents such as hydrocarbon or aromatic solvents may be employed as diluents. However, it is preferable, when taking into consideration a heat treatment carried out after the formation of coating film, to employ fire-retardant and thermally stable solvents, e.g., carbon tetrachloride and trichloroethylene. In place of the above-described silicone coating agents, fluorine coating agents may also be employed in the present invention. For example, fluorine coating agents such as JX-900 and FC-721 (manufactured by Sumitomo 3M Limited) and solutions obtained by diluting these coating agents with chlorine solvents are effective in forming a coating film on AMAS which is used in the present invention. In general, the coating agent content in the coated bactericidal AMAS of the present invention is preferably selected so as to fall within the range from 0.01 to 15%, more preferably from 0.1 to 10%, although the preferable range depends on the kind of the coating agent employed. In the antifungal and antibacterial polymer according to the present invention which contains the above-described coated AMAS carrying bactericidal or antibacterial metal ions, the AMAS content is generally selected so as to fall within the range from 0.005 to 50% by weight (on an anhydrous basis), although the range depends on the kind and properties of the polymer employed. The bactericidal metal ion content in the coated AMAS is determined on the basis of the aforementioned bactericidal metal content in the non-coated AMAS. The coated AMAS solid particles holding metal ions having a bactericidal action may be mixed with an organic polymer in any step before the polymer is molded on the basis of the above-described mixing of the uncoated AMAS solid particles holding bactericidal metal ions.

Primary features and advantages of the bactericidal or antibacterial polymer containing AMAS according to the present invention may be summarized as follows.

(a) Since antibacterial AMAS used in the present invention is an inorganic substance, mixing of an appropriate amount of AMAS with polymers causes no structure deterioration in most polymers.

(b) Mixing of coated antibacterial AMAS with a polymer enables prevention of any interaction between the AMAS and the polymer or other coexisting substances.

(c) Bactericidal polymers according to the present invention advantageously exhibit excellent antibacterial and antifungal actions against general bacteria and fungi for a long period of time.

(d) Bactericidal AMAS has substantially no toxicity, and elution and vaporization of the AMAS from a polymer which contains the same are extremely small in amount and therefore give rise to no problem. Accordingly, the safety level of the AMAS is advantageously high.

(e) A polymer containing bactericidal AMAS according to the present invention is not only per se made antibacterial but also allowed to exhibit an antibacterial or bactericidal action with respect to the atmosphere (gaseous phase or liquid phase) which is in contact with the polymer.

(f) In many polymers, it is only necessary to employ a relatively small amount of bactericidal AMAS so as to be contained in a polymer in order to achieve a predetermined antibacterial effect, advantageously.

(g) Bactericidal AMAS used in the present invention exhibits excellent dispersibility and is chemically stable, so that it is readily mixed with a polymer.

(h) The bactericidal or antibacterial power of the polymer according to the present invention only slightly changes with time, and the polymer exhibits not only an antibacterial or bactericidal action against bacteria but also a strong antifungal power against fungi for a long period of time, advantageously.

AMAS which is employed as a material in production of an antibacterial composition according to the present invention is amorphous as has already been described. Production examples of AMAS will be explained below.

PRODUCTION EXAMPLE 1 (AMAS)

This example relates to the production of an AMAS having a molar ratio of $SiO_2/Al_2O_3 \cong 2.5$.

Solution-A: 1.73 kg of 49% sodium hydroxide solution (specific gravity=1.51) and water were added to 1.06 kg of aluminum hydroxide [$Al(OH)_3 \cdot xH_2O$; $x \cong 0$], and the resultant mixture was heated to obtain a solution. Then, water was further added to this solution so that the whole quantity of the solution was eventually 4.5 l. A trace amount of suspended matter in the solution was filtered out to prepare a transparent solution (Solution-A).

Solution-B: 0.13 kg of 49% sodium hydroxide solution (specific gravity=1.51) and water were added to 4.4 kg of sodium silicate (JIS-No.3; specific gravity=1.4; $Na_2O$=9.5%; $SiO_2$=29%) so that the whole quantity of the mixture was 4.5 l. A trace amount of a suspended matter in this solution was filtered out to prepare a transparent solution (Solution-B).

Solution-C: Water was added to 1.6 kg of 49% sodium hydroxide solution (specific gravity=1.51) so that the whole quantity of the mixture was 7.8 l (Solution-C).

Solution-C was placed in a reaction tank and maintained under stirring at 350 rmp while being heated at 38°±2° C. After Solution-A and Solution-B had been maintained at around 40° C., they were simultaneously but individually poured into the reaction tank containing Solution-C in such a manner that the pouring of the solutions was completed during a period of 55 minutes. After the completion of the mixing of the material solutions, the slurry-containing liquid was maintained for 4 hours under stirring at 270 rpm at about 40° C. to age the prepared AMAS. After the completion of the aging, the AMAS was filtered by means of centrifugal separation and then rinsed with hot water. This rinsing was effected until the pH of the filtrate reached 10.6. After the completion of the rinsing, the AMAS was dried at 100° to 110° C. and then pulverized to obtain about 1.99 kg of a dried AMAS fine powder as a final product.

Analysis of Production Example 1:
Yield of dried AMAS fine powder: about 1.99 kg
Chemical composition: $1.10Na_2O \cdot Al_2O_3 \cdot 2.51SiO_2 \cdot xH_2O$
Dav: 0.2 μm
SSA: 22 m²/g

PRODUCTION EXAMPLE 2 (AMAS)

This example relates to the production of an AMAS having a molar ratio of $SiO_2/Al_2O_3 \cong 3.2$.

Solution-A: 2.9 kg of 49% sodium hydroxide solution (specific gravity=1.51) and water were added to 2.53 kg of aluminum hydroxide [$Al(OH)_3 \cdot xH_2O$; $x \cong 0$], and the resultant mixture was heated to obtain a solution. Water was further added to this solution so that the whole quantity of the mixture was eventually 6.5 l. A trace amount of suspended matter in the solution was filtered out to prepare a transparent solution (Solution-A).

Solution-B: Water was added to 5.5 kg of sodium silicate solution (JIS-No. 3; specific gravity=1.4; $Na_2O$=9.5%; $SiO_2$=29%) so that the whole quantity of the mixture was eventually 7.3 l. A trace amount of suspended matter in the solution was filtered out to prepare a transparent solution (Solution-B).

Solution-C: 0.54 kg of 49% sodium hydroxide solution (specific gravity=1.51) was diluted with water so that the whole quantity of the solution was 3.2 l (Solution-C).

Solution-C was placed in a reaction tank and maintained under stirring at 500 rpm while being heated at about 35° C. Solution-A and Solution-B which had been heated at about 35° C. were simultaneously but individually poured into the reaction tank containing Solution-C in such a manner that the pouring of these solutions was completed during a period of 1 hour.

After the completion of mixing of the material solutions, the slurry-containing liquid was maintained for 4 hours under stirring at 350 rpm at about 35° C., and the prepared AMAS was then filtered by means of centrifugal separation. The AMAS was rinsed with hot water in a manner similar to that in the above-described example. The rinsed AMAS was then dried at 100° to 110° C. and pulverized to obtain about 3.7 kg of a dried AMAS fine powder as a final product.

Analysis of Production Example 2:
Yield of dried AMAS fine powder: about 3.7 kg
Chemical composition: $1.03Na_2O.Al_2O_3.3.24SiO_2.xH_2O$
Dav: 0.2 μm
SSA: 56 m²/g

PRODUCTION EXAMPLE 3 (AMAS)

This example relates to the production of an AMAS material which is required in preparation of an antibacterial and bactericidal amorphous aluminosilicate composition according to the present invention having a molar ratio of $SiO_2/Al_2O_3 \cong 6$.

Solution-A: 3.6 kg of 49% sodium hydroxide solution (specific gravity=1.51) and water were added to 1.37 kg of aluminum hydroxide [$Al(OH)_3.xH_2O$; $x\cong 0$], and the resultant mixture was heated to obtain a solution. Water was further added to this solution so that the whole quantity of the solution was 3.6 l. A trace amount of suspended matter in the solution was filtered out to prepare a transparent solution (Solution-A).

Solution-B: Water was added to 12.5 kg colloidal silica (trade name: Snowtex-30) so that the whole quantity of the solution was 10.8 l. A trace amount of suspended matter in the solution was filtered out to prepare a transparent solution (Solution-B).

Solution-C: Water was added to 14.9 kg of 49% sodium hydroxide solution (specific gravity=1.51) so that the whole quantity of the solution was 7.2 l (Solution-C).

Solution-C was placed in a reaction tank and maintained under stirring at 300 rpm while maintaining the temperature of Solution-C at 30° C. Solution-A and Solution-B which had been maintained at about 30° C. were simultaneously but individually poured into the reaction tank containing Solution-C in such a manner that the pouring of these solutions was completed during a period of 45 minutes. After the completion of mixing of the material solutions, the slurry-containing liquid was maintained for 2 hours and 50 minutes under stirring at 400 rpm and at about 30° C. to age AMAS, and the prepared AMAS was then filtered by means of centrifugal separation. The resultant solid phase was rinsed with hot water (until the ph of the filtrate reached 10.8) in a manner similar to that in the above-described production example. The rinsed AMAS was then dried at 100° to 110° C. and subsequently pulverized to obtain 4.08 kg of a dried AMAS fine powder as a final product.

Analysis of Production Example 3:
Yield of dried AMAS fine powder: 4.08 kg
Chemical composition: $1.42Na_2O.Al_2O_3.6.04SiO_2.xH_2O$
Dav: 0.2 μm or less
SSA: 139 m²/g The AMAS's which are employed as materials for the present invention and which are respectively obtained in accordance with the above-described Production Examples 1 to 3 are amorphous and porous, and they are fine powders each having SSA of 20 m²/g or more and Dav of 1 μm or less. The respective chemical compositions of the AMAS's obtained by Production Examples 1 to 3 are such as those described above, and all the AMAS's have a preferable and sufficient exchange capacity to prepare an antibacterial composition according to the present invention. In addition, exchange-ions ($Na^+$) of the above-described materials and antibacterial metal ions are exchanged at extremely high speed, and AMAS as a parent body and antibacterial metal ions are joined together with extremely high bonding strength.

The following is a description of examples which relate to the process for preparing AMAS compositions having antibacterial and bactericidal actions according to the present invention.

PRODUCTION EXAMPLE 4

This example relates to the process for preparing an Ag-AMAS composition ($SiO_2/Al_2O_3=2.51$) according to the present invention which contains silver. About 250 g of the dried AMAS powder ($1.10Na_2O.Al_2O_3.2.51SiO_2.xH_2O$) produced in the above-described Production Example 1 was collected, and 500 ml of any one of the solution of the 0.05M $AgNO_3$ (Production Example 4-A), 0.3M $AgNO_3$ (Production Example 4-B) and 0.6M $AgNO_3$ (Production Example 4-C) was added to the above-described AMAS powder. The resultant mixture was maintained for 5 hours under stirring at 350 rpm and at room temperature, whereby some of the exchangeable $Na^+$ in the AMAS were exchanged for $Ag^+$. After the completion of this ion exchange reaction, the Ag-AMAS was filtered, and the resultant solid phase was rinsed to remove any excessive $Ag^+$ present in the solid phase. The rinsed Ag-AMAS was then dried at 100° to 110° C. and subsequently pulverized to obtain a dried Ag-AMAS fine powder. The results of this example are shown in Table 1 below. The average particle diameters (Dav) of the Ag-AMAS fine powders obtained in this example were 0.24 μm (4-a), 0.22 μm (4-B) and 0.26 μm (4-C), respectively.

TABLE 1

Preparation of Ag-AMAS composition according to the present invention containing silver (Production Example 4)

| Example No. | AMAS as raw material (Production Example 1 | Concentration and amount of $AgNO_3$ solution | Yield of Ag-AMAS (dry product) | Ag content in Ag-AMAS | |
|---|---|---|---|---|---|
| | | | | Ag % (dry basis) | Ag % (anhydrous basis) |
| 4-A | about 250 g | 0.05 M $AgNO_3$ (500 ml) | 220 g | 1.03 | 1.11 |
| 4-B | " | 0.3 M $AgNO_3$ (500 ml) | 202 g | 6.02 | 6.90 |
| 4-C | " | 0.6 M $AgNO_3$ | 218 g | 11.35 | 13.06 |

TABLE 1-continued

Preparation of Ag-AMAS composition according to
the present invention containing silver (Production Example 4)

| Example No. | AMAS as raw material (Production Example 1) | Concentration and amount of AgNO$_3$ solution | Yield of Ag-AMAS (dry product) | Ag content in Ag-AMAS | |
|---|---|---|---|---|---|
| | | | | Ag % (dry basis) | Ag % (anhydrous basis) |
| | | (500 ml) | | | |

PRODUCTION EXAMPLE 5

This example relates to the preparation of a Cu-AMAS composition (SiO$_2$/A$_2$O$_3$=3.24) according to the present invention which contains copper. About 100 g (Production Example 5-A) or about 250 g (Production Example 5-B) of the dried AMAS powder (1.03Na$_2$O.Al$_2$.3.24SiO$_2$.xH$_2$O) produced in the above-described Production Example 2 was collected, and 500 ml of 0.02M Cu(NO$_3$)$_2$ solution was added to the former AMAS, or 500 ml of 0.6M Cu(NO$_3$)$_2$ solution was added to the latter AMAS. The former or latter solution was further diluted with water and maintained as shown in Table 2. The resultant mixture was then maintained for 6 hours under stirring at 360 rpm, whereby some of the exchangeable Na$^+$ in the AMAS were exchanged for Cu$^{2+}$ (ion exchange at ordinary temperature). After the completion of the ion exchange operation, the Cu-AMAS was filtered, and the resultant solid phase was rinsed to remove any excessive Cu$^{2+}$ present in the solid phase. The rinsed Cu-AMAS was then dried at 100° to 110° C. and subsequently pulverized to obtain a dried Cu-AMAS fine powder.

The results of this example are shown in Table 2 below. The Cu-AMAS's obtained in this example had an average particle diameter (Dav) of 0.2 μm, while the specific surface area (SSA) of Production Example 5-A was 56 m$^2$/g, and SSA of Production Example 5-B was 59 m$^2$/g.

PRODUCTION EXAMPLE 6

This example relates to preparation of a Zn-AMAS composition (SiO$_2$/Al$_2$O$_2$.6.04SiO$_2$.xH$_2$O) according to the present invention which contains zinc. About 250 g of the dried AMAS powder (1.42Na$_2$O.Al$_2$O$_3$.6.04SiO$_2$.xH$_2$O) produced in the above-described Production Example 3 was collected, and 500 ml of either 0.1M Zn(NO$_3$)$_2$ (Production Example 6-A) or 1.0M Zn(NO$_3$) (Production Example 6-B) was added to the AMAS. The resultant mixture was maintained for 7 hours under stirring at 400 rpm, whereby some of the exchangeable Na$^+$ in the AMAS were exchanged for Zn$^{2+}$ (ion exchange at ordinary temperature). The produced Zn-AMAS was then filtered, and the resultant solid phase was rinsed to remove any excessive Zn$^{2+}$ present in the solid phase. The rinsed Zn-AMAS was dried at 100° to 110° C. and then pulverized to obtain a dried Zn-AMAS fine powder.

The results of this example are shown in Table 3 below. All the Zn-AMAS's obtained in this example had an average particle diameter (Dav) of 0.6 μm, while they had substantially the same specific surface area, that is, Production Example 6-A had SSA of 140 m$^2$/g and Production Example 6-B had SSA of 141 m$^2$/g.

TABLE 3

Preparation of Zn-AMAS composition according to
the present invention containing zinc (Production Example 6)

| Example No. | AMAS as raw material (Production Example 3) | Concentration and amount of Zn(NO$_3$)$_2$ | Yield of Zn-AMAS (dry product) | Zn content in Zn-AMAS | |
|---|---|---|---|---|---|
| | | | | Zn % (dry basis) | Zn % (anhydrous basis) |
| 6-A | about 250 g | 0.1 M Zn(NO$_3$)$_2$ (500 ml) | 230 g | 1.64 | 1.77 |
| 6-B | " | 1.0 M Zn(NO$_3$)$_2$ (500 ml) | 243 g | 4.51 | 5.02 |

Production Examples 7 to 12

Production Examples 7 to 12 respectively show preparation examples for Bi-AMAS (Dav=0.1 μm), Cr-AMAS (Dav=0.1 μm), Sn-AMAS (Dav=0.2 μm), Hg-AMAS (Dav=0.2 μm), Pb-AMAS (Dav=0.4 μm) and Cd-AMAS (Dav=0.2 μm) (see Table 4).

TABLE 2

Preparation of Cu-AMAS composition according to
the present invention containing copper (Production Example 5)

| Example No. | AMAS as raw material (Production Example 2) | Concentration and amount of Cu(NO$_3$)$_2$ | Whole quantity | Yield of Cu-AMAS (dry product) | Cu content in Cu-AMAS | |
|---|---|---|---|---|---|---|
| | | | | | Cu % (dry basis) | Cu % (anhydrous basis) |
| 5-A | about 100 g | 0.02 M Cu(NO$_3$)$_2$ (200 ml) | about 360 ml | 97 g | 0.27 | 0.31 |
| 5-B | about 250 g | 0.6 M Cu(NO$_3$)$_2$ (500 ml) | about 500 ml | 245 g | 8.33 | 9.25 |

TABLE 4

Preparation of antibacterial AMAS compositions according to the present invention (Production Examples 7-12)

| Example No. | Dry powder of AMAS as raw material* | Concentration and amount of salt solution | Yield of antibacterial AMAS (dry product) | Antibacterial metal content in antibacterial AMAS M % (dry basis) | Antibacterial metal content in antibacterial AMAS M % (anhydrous basis) |
|---|---|---|---|---|---|
| 7 | about 50 g | 0.05 M $Bi(NO_3)_2$** (150 ml) | Bi-AMAS (41 g) | Bi (3.85) | Bi (4.30) |
| 8 | " | 0.05 M $Cr(NO_3)_2$ (150 ml) | Cr-AMAS (46 g) | Cr (2.29) | Cr (2.53) |
| 9 | " | 0.05 M $SnCl_2$** (150 ml) | Sn-AMAS (42 g) | Sn (1.83) | Sn (1.10) |
| 10 | " | 0.05 M $Hg(NO_3)_2$ (150 ml) | Hg-AMAS (45 g) | Hg (5.24) | — |
| 11 | about 100 g | 0.3 M $Pb(NO_3)_2$ (300 ml) | Pb-AMAS (75 g) | Pb (5.66) | Pb (5.97) |
| 12 | " | 0.3 M $Cd(NO_3)_2$ (300 ml) | Cd-AMAS (98 g) | Cd (4.17) | Cd (4.41) |

*AMAS as raw material: $0.86Na_2O \cdot Al_2O_3 \cdot 2.56SiO_2 \cdot xH_2O$; SSA = 29 $m^2/g$

**Small amounts of $HNO_3$ and HCl are resprectively added to 0.05 M $Bi(NO_3)_2$ and 0.05 M $SnCl_2$ solutions so as to be slightly acidic to prevent deposition of a basic salt or an oxide in the AMAS phase by hydrolysis when ion exchange is carried out.

As starting materials, dried products of AMAS's with SSA of 29 $m^2/g$ which had respective compositions shown in Table 4 were employed. In each of Production Examples 7 to 10, about 50 g of AMAS and 150 ml of 0.05M salt solution were used, while, in each of Production Examples 11 and 12, about 100 g of AMAS and 300 ml of 0.3M salt solution were used, and each mixture was maintained for 4 hours and 20 minutes under stirring at 360 rpm, whereby some of $Na^+$ of each AMAS were replaced by antibacterial metal ions such as those shown in Table 4 (ion exchange at ordinary temperature), thus obtaining an AMAS composition having both antibacterial and bactericidal actions. Rinsing and drying of the M-AMAS's shown in Table 4 were carried out in the same way as that in the above-described examples.

PRODUCTION EXAMPLE 13

This example relates to the production of an AMAS. In this example, the following solutions were prepared as material solutions.

Solution-A: 3.45 kg of 49% sodium hydroxide solution (specific gravity=1.51) and water were added to 2.12 kg of aluminum hydroxide [$Al(OH)_3 \cdot xH_2O$; $x \cong 0$], and the resultant mixture was heated to obtain a solution. Water was further added to this solution so that the whole quantity of the solution was eventually 9.9 l. A trace amount of suspended matter in the solution was filtered out to prepare a transparent solution.

Solution-B: 0.25 kg of 49% sodium hydroxide solution (specific gravity=1.51) and water were added to 8.7 kg of sodium silicate (JIS-No.3; specific gravity=1.4; $Na_2O$=9.5%; $SiO_2$=29%) so that the whole quantity of the mixture was 8.9 l. A trace amount of suspended matter in this solution was filtered out to prepare a transparent solution.

Solution-C: Water was added to 3.1 kg of 49% sodium hydroxide solution (specific gravity=1.51) so that the whole quantity of the mixture was 15.6 l (the alkalinity of Solution-C=2.42N). Solution-C (15.6 l) was placed in a reaction tank and maintained under stirring at 350 rpm while being heated at 40° C. Solution-A (about 40° C.; 8.9 l) and Solution-B (about 40° C.; 8.9 l) were simultaneously but individually poured into the reaction tank containing Solution-C in such a manner that the pouring of the solutions was completed during a period of 100 minutes. During the addition of Solution-A and Solution-B into Solution-C, the molar ratio of $SiO_2/Al_2O_2$ in the resulting mixture was maintained at 3.38 (Si/Al=1.69) throughout the pouring operation. In this example, the molar ratio of $Na_2O/Al_2O_3$ and that of $Na_2O/SiO_2$ upon completion of the mixing of the material solutions were 4.43 and 1.31, respectively. After the completion of the mixing of the material solutions, the slurry-containing liquid was maintained for 5 hours under stirring at 250 rpm at about 40° C. to age the prepared AMAS. After the completion of the aging, the AMAS was filtered by means of centrifugal separation and then rinsed with hot water. This rinsing was effected until the pH of the filtrate reached 10.5. After the completion of the rinsing, the AMAS was dried around 100° C. and then pulverized using a Braun pulverizer to obtain about 4.1 kg of a dried AMAS fine powder as a final product.

Examples of the present invention will be described hereinunder. It should be noted that the present invention is not necessarily limited to Examples and various changes and modifications may be imparted thereto without departing from the gist of the invention. In Examples, evaluation of the bactericidal or antibacterial effect was made by the following testing methods. The fungal resistance test in Examples was carried out in accordance with the ASTM G-21 testing method using culture media having a chemical composition which consists essentially of $KH_2PO_4$ (0.7 g), $K_2HPO_4$ (0.7 g), $MgSO_4 \cdot 7H_2O$ (0.7 g), $NH \cdot NO_3$(1.0 g), NaCl (0.005 g), $FeSO_4 \cdot 7H_2O$ (0.002 g), $ZnSO_4 \cdot 7H_2O$ (0.002 g), $MnSO_4 \cdot 7H_2O$ (0.001 g), agar (15 g) and pure water (1,000 ml). As test fungi, the following five types of fungi were employed: *Aspergillus niger* (ATCC 9642); *Penicillium funiculosum* (ATCC 9644); *Chaetomium globosum* (ATCC 6205); Trichoderma T-1 (ATCC 9645); and *Aureobasidium pullulans* (ATCC 9348). These fungi were mixedly inoculated into culture media. Cultivation was carried out for 30 days at a relative humidity (R.H.) of 85 to 95%. Evaluation of the results of the test was made in accordance with the following five ranks.

| Evaluation marks | Remarks |
|---|---|
| 0 | No fungi grow |
| 1 | Grow slightly (10% or less) |
| 2 | Grow a little (10–30%) |

-continued

| Evaluation marks | Remarks |
|---|---|
| 3 | Grow intermediately (30–60%) |
| 4 | Grow flourishingly (60–100%) |

In relation to the evaluation of the antibacterial power, the change with time in the number of individuals of bacteria and fungi was measured by the following method.

(i) Preparation of Bacterial Solution

Bacteria were pre-cultivated in a common bouillon culture medium for one night at 35° C. and then appropriately diluted with a sterilized physiological saline to prepare an inoculation bacterial solution.

(ii) Preparation of Spore Suspension

Fungi were pre-cultivated in a culture medium until spores were satisfactorily formed. The spores were then suspended in a 0.005% dioctyl sodium sulfosuccinate solution and the suspension was appropriately diluted with a sterilized physiological saline to prepare an inoculation spore suspension.

(iii) Testing Procedure

Each of the samples was put in a 300-ml Erlenmeyer flask containing 40 ml of sterilized physiological saline. The inoculation bacterial solution and the inoculation spore suspension were respectively put in the flasks so that the number of individuals of each of the bacteria or fungi was about $10^4$ per milliliter. The flasks were shaken at room temperature, and the numbers of individuals surviving were measured in accordance with passage of time. The measurement was carried out after a predetermined period of time had elapsed. As to the bacteria, the number of individuals surviving was measured after 2 days of cultivation in an SCDLP agar medium at 35° C.; as to the fungi, the number of individuals surviving was measured after 7 days of cultivation in a GPLP agar medium at 25° C.

In addition to the above-described antibacterial test, measurement of the death rate was carried out by the following method.

(i) Bacteria: One milliliter of a suspension ($10^\circ$ individuals per milliliter) was added into and mixed with 9 ml of a suspension of a test substance (100 mg/ml), and the mixture was maintained for 24 hours at 37° C. to cause a reaction. Then, 0.1 ml of the mixture was dispersed in a Mueller Hinton medium, and this was maintained for 24 hours at 37° C. Then, the number of individuals surviving was measured to obtain the death rate.

(ii) Fungi: One milliliter of a spore suspension ($10^\circ$ individuals per milliliter) was added into and mixed with 9 ml of a suspension of a test substance (100 mg/ml), and the mixture was maintained for 24 hours at 30° C. to cause a reaction. Then, 0.1 ml of the mixture was dispersed in a Sabouraud agar medium, and this was maintained for 48 hours at 30° C. Then, the number of individuals surviving was measured to obtain the death rate.

The following cultures were employed to measure the change with time in the number of individuals of each of the bacteria and fungi and to obtain the death rate:

*Aspergillus niger* (ATCC 9642)
*Aspergillus flavus* (ATCC 10836)
*Staphylococcus aureus* (IFO 13276)
*Escherichia coli* (IFO 3301)
*Salmonella typhymurium* (laboratory preservation culture)
*Vibrio paraphaemoliticus* (IFO 12711)

EXAMPLE 1

This example relates to the production of an AMAS having a bactericidal action and the trial production of a polypropylene (PP) molded product containing said AMAS.

Two liters of water was added to a dried AMAS powder $1.1Na_2O.Al_2O_3.2.9SiO_2$; average particle diameter Dav=0.2 μm) to obtain a slurry, and 2 l of a 0.1M $AgNO_3-0.3M\ Cu(NO_3)_2$ mixed solution was added to the slurry. The mixture was maintained for 3 hours under stirring at 40° to 50° C. to cause an ion exchange reaction. After the completion of the reaction, the reaction product was filtered and then rinsed to remove excessive silver and copper ions from the solid phase. The rinsed product was dried at 100° to 110° C. and then pulverized into a fine powder using a pulverizer. By the above-described ion exchange reaction, it was possible to obtain 0.88 kg of bactericidal dried AMAS powder [Ag=3.01%; Cu=4.84% (on an anhydrous basis); average particle diameter Dav=0.32 μm; specific surface area SSA=43 $m^2/g$].

The bactericidal AMAS prepared by the above-described process was heated to about 320° C. to remove water therefrom until the water content reached 2% or less. The dried together in a predetermined weight ratio to prepare mixtures having various chemical compositions. Each of the mixtures was heated to about 180° C. so as to be melted and intimately mixed in this molten state. The resultant mixture was then pressurized under a load of about 20 kg/cm, G so as to be shaped into a plate (100×100 mm; thickness=1.5 mm) as an article made on a trial basis.

The AMAS-PP plate thus obtained was cut to prepare a test specimen (50×50 mm; thickness=1.5 mm), and an antibacterial power evaluation test was carried out by the above-described method. Table 5 exemplarily shows the change with time in the number of individuals of each of the inoculated fungi and bacteria. From the comparison between the test specimen 1-1 (Ag=0.14%; Cu=0.25%) containing about 5% of AMAS and the test specimen 1-BL (a plate formed from PP containing no antibacterial agent; prepared for a blank test), it is clear that the bactericidal PP polymer according to the present invention has a bactericidal effect against fungi (*Aspergillus flavus*). It is also clear that the PP polymer of the present invention has a bactericidal effect against general bacteria from the comparison as to the bactericidal effect against Staphyloooocous aureus between the test specimen 1-2 (Ag=0.061%; Cu=0.10%) containing about 2% of AMAS and the test specimen 1-BL.

TABLE 5

| Number of test specimen | Change with time in number of individuals of inoculated fungus and bacteria (Example 1) | | | | |
|---|---|---|---|---|---|
| | Test fungus and bacteria | Shaking time (hr) | | | |
| | | 0 | 5 | 24 | 48 |
| 1-1 | *Aspergillus flavus* | $4.1 \times 10^4$ | $3.9 \times 10^3$ | $1.3 \times 10^3$ | $6.3 \times 10^1$ |

TABLE 5-continued

| Number of test specimen | Change with time in number of individuals of inoculated fungus and bacteria (Example 1) | | | | |
|---|---|---|---|---|---|
| | Test fungus and bacteria | Shaking time (hr) | | | |
| | | 0 | 5 | 24 | 48 |
| 1-BL (blank test) | " | $4.3 \times 10^4$ | $8.8 \times 10^3$ | $3.5 \times 10^3$ | $2.8 \times 10^3$ |
| 1-2 | Staphylococcus aureus | $5.5 \times 10^4$ | $1.3 \times 10^4$ | $4.2 \times 10^2$ | $1.8 \times 10^1$ |
| 1-BL (blank test) | " | $3.8 \times 10^4$ | $9.2 \times 10^3$ | $2.3 \times 10^3$ | $4.7 \times 10^2$ | unit: Number of individuals surviving in 1 ml of test solution
Specimen: 50 × 50 mm; thickness = 1.5 mm

EXAMPLE 2

This example relates to the production of an AMAS having a bactericidal action and the trial production of a polypropylene (PP) molded product containing said AMAS. In this example, however, an AMAS having a different composition from that of the AMAS in Example 1 was prepared, and a PP polymeric molded product was made on a trial basis using this AMAS. In addition, the antibacterial power test was carried out using the PP polymeric molded product.

Five liters of water was added to a dried AMAS powder ($1.2Na_2O.Al_2O_3.6.4SiO_2$; average particle diameter Dav=0.1 μm) to obtain a slurry, and 6.7 l of a 0.1M $AgNO_3$−0.55M $Cu(NO_3)_2$ mixed solution was added to the slurry. The mixture was maintained for 5 hours under stirring at 20° to 25° C. to cause an ion exchange reaction. After the completion of the reaction, the reaction product was filtered and then rinsed to remove excessive silver and copper ions from the solid phase. The rinsed product was dried at 100° to 110° C. and then pulverized into a fine powder using a pulverizer. By the above-described ion exchange reaction of $Na^+$ in the solid phase and $Ag^+$ and $Cu^{2+}$ in the aqueous solution phase, it was possible to obtain 2.98 kg of bactericidal dried AMAS powder [Ag=2.70%; Cu=3.86% (on an anhydrous basis); molar ratio of $SiO_2/Al_2O_3$=6.4; average particle diameter Dav=0.15 μm; specific surface area SSA=116 $m^2/g$].

The bactericidal AMAS prepared by the above-described process was heated to about 320° C. to remove water therefrom until the water content reached 2% or less. The dried product and PP resin in the form of powder were mixed together in a predetermined weight ratio to prepare mixtures having various chemical compositions. Each of the mixtures was heated to about 180° C. so as to be melted and intimately mixed in this molten state. The resultant mixture was then pressurized under a load of about 20 kg/cm, G so as to be shaped into a plate (100×100 mm; thickness=1.5 mm) as an article made on a trial basis.

The AMAS-PP plate thus obtained was cut to prepare a test specimen (50×50 mm; thickness=1.5 mm), and as an antibacterial power evaluation test, measurement of the death rate was carried out by the above-described method. Table 6 exemplarily shows some of the results of the test. The test specimen 2-1 (Ag=0.0029%; Cu=0.004%) contained about 0.1% of the bactericidal AMAS prepared as described above, while the test specimen 2-2 (Ag=0.052%; Cu=0.073%) contained about 2% of the bactericidal AMAS. The test specimen 2-BL was a plate containing PP only which was prepared for a blank test. The death rate measured when the test specimen 2-1 was used against Escherichia coli reached 88% after 24 hours had elapsed after the start of the reaction at 37° C., whereas the death rate in the case of the test specimen 2-BL for a blank test was 0%. The death rate measured when the test specimen 2-2 was used against Salmonella typhymurium in relation to food poisoning reached 100% after 24 hours had elapsed after the start of the reaction at 37° C., whereas, the death rate in the case of the test specimen 2-BL for a blank test was 0%. It is clear from the above-described experimental example that the PP polymer containing a small amount of AMAS according to the present invention has a bactericidal effect. This also confirms that addition of a very small amount of antibacterial or bactericidal AMAS of the present invention to a polymer provides a satisfactory effect.

TABLE 6

| Measurement of death rate (Example 2) Specimen: 50 × 50 mm; thickness = 1.5 mm | | |
|---|---|---|
| Number of test specimen | Test bacteria | Death rate* (%) |
| 2-1 | Escherichia coli | 88 |
| 2-BL (blank test) | " | 0 |
| 2-2 | Salmonella typhymurium | 100 |
| 2-BL (blank test) | " | 0 |

*Death rate measured after 24 hours of reaction at 37° C.

EXAMPLE 3

The examples relates to the trial production of a polyvinyl chloride (PVC) containing AMAS, having a bactericidal action and the evaluation of the antibacterial power thereof. In this example, the AMAS [Ag=2.70%; Cu=3.86% (on an anhydrous basis); molar ratio of $SiO_2/Al_2O_3$=6.4; average particle diameter Dav=0.15 μm; specific surface area SSA=116 $m^2/g$] which was produced in Example 2 on a trial basis was employed as an antibacterial agent.

The above-described bactericidal AMAS was heated at about 350° C. to reduce the water content to 2% or less and then added to PVC to prepare a sheet eventually. More specifically, 60 parts of DOP (di-2-ethyl-hexyl phthalate) as a plasticizer was added to 100 parts of PVC [Nipolit SL (general-purpose grade; polymerization degree=1000) manufactured by Chisso Corporation], and small amounts of a stabilizer and a gelatinizing agent were further added thereto to obtain a mixture, which was then mixed with a predetermined amount of AMAS having a water content 2% or less which had been produced in Example 2 on a trial basis. The resultant mixture was kneaded at about 140° C. by means of a mixing roll to obtain an intimate mixture, which was then shaped into a sheet having a thickness of 5 mm.

The resultant AMAS-PVC sheet is cut to prepare a test specimen (15×35; thickness=5 mm). As an antibacterial power evaluation test, measurement of the change with time in the number of individuals of each of the inoculated bacteria was carried out by the above-described method using the prepared test specimen. The test specimen 3-1[Ag=0.26%; Cu=0.38%; trace components of 1% or less (Zn, Ba and Ca)] exemplarily shown in Table 7 was the test specimen prepared form the PVC sheet containing about 10% of bactericidal AMAS produced in Example 3 on a trial basis. As will be clear from Table 7, the number of individuals of *Staphylococcus aureus* as remarkably reduced by the use of the test specimen 3-1, and the number of individuals reached 0 after 24 hours had elapsed after the start of the reaction. In the case of a test specimen 3-BL [for a blank test; a sheet containing PVC only; trace components of 1% or less (Zn, Ba and Ca)] which contained the same type of PVC as that of the test specimen 3-1, the number of individuals of the bacteria measured after 24 hours had elapsed after the start of the reaction was $1.9 \times 10^3$ and was only slightly reduced to $5.4 \times 10$, after 48 hours of shaking. From the comparison between these two test specimens, it will be clear that the PVC sheet containing antibacterial AMAS has an antibacterial effect.

TABLE 7

| Number of test specimen | Change with time in number of individuals of inoculated bacteria (Example 3) | | | | |
|---|---|---|---|---|---|
| | Test bacteria | Shaking time (hr) | | | |
| | | 0 | 5 | 24 | 48 |
| 3-1 | *Staphylococcus aureus* | $5.3 \times 10^4$ | $1.9 \times 10^2$ | 0 | 0 |
| 3-BL | " | $3.1 \times 10^4$ | $2.2 \times 10^4$ | $1.9 \times 10_3$ | $5.4 \times 10^2$ | unit: Number of individuals surviving in 1 ml of test solution
Specimen: PVC sheet (15 × 35 mm; thickness = 5 mm)

Next, the AMAS-PVC sheet produced in this example on a trial basis was cut to prepare a test specimen (50×50 mm; thickness=5 mm) having the same chemical composition as that of the test specimen 3-1, and the aforementioned five kinds of fungi were mixedly inoculated on this test specimen to carry out a fungal resistance test in accordance with the aforementioned ASTM G-21. Cultivation in this case was carried out for 30 days at a relative humidity (R.H.) of 85 to 95%. The result of this test was 0 according to the above-described evaluation mark. In other words, it has been confirmed that no growth of fungi was found on this PVC sheet.

EXAMPLE 4

This examples relates to the trial production of a polyvinyl chloride (PVC) containing AMAS having a bactericidal action and the evaluation of the antibacterial power thereof. In this example, the AMAS [Ag=2.70%; Cu=3.86% (on an anhydrous basis); molar ratio of $SiO_2/Al_2O_3=6.4$; average particle diameter Dav=0.15 μm; specific surface area SSA=116 $m^2/g$] which was produced in Example 2 on a trial basis was employed as an antibacterial agent. In this example, a PVC molded product containing 7 to 15% of the above-described antibacterial agent was produced on a trial basis, and test specimens were prepared therefrom to establish whether or not an inhibition zone was formed against bacteria and fungi.

The above-described AMAS was heated at about 350° C. to reduce the water content to 2% or less and then added to PVC to prepare a sheet eventually. More specifically, 60 parts of DOP (di-2-ethylhexyl phthalate) as a plasticizer was added to 100 parts of PVC [Nipolit SL (general-purpose grade; polymerization degree=1000) manufactured by Chisso Corporation], and small amounts of a stabilizer and a gelatinizing agent were further added thereof to obtain a mixture, which was then mixed with a predetermined amount of AMAS having a water content 2% or less which had been produced in Example 2 on a trial basis. The resultant mixture was kneaded at about 140° C. by means of a mixing roll to obtain an intimate mixture, which was then shaped into a sheet having a thickness of 5 mm. In this example, PVC sheets respectively containing 7, 0, 14 and 15% of the above-described antibacterial agent were prepared.

The test to establish whether or not an inhibition zone was formed was carried out by the following method. A suspension of a test substance was prepared at a concentration of 100 mg/ml, and a disk was impregnated with this suspension. As to the culture medial, Mueller Hinton media were employed for bacteria, while Sabouraud agar media were used for fungi. Each of the test bacteria or fungi was suspended in physiological saline at a concentration of $10^3$ individuals per ml, and 0.1 ml of this suspension was dispersed in a culture medium by means of a Conradi bar. Then, a test disk was stuck on this culture medium. As to bacteria, the test disk was maintained in the above-described state for 18 hours at 37° C., and observation was then made as to whether or not an inhibition zone was formed on the disk. As to fungi, judgment was made after 1 week had elapsed with the temperature maintained at 30° C. The results of the test are shown in Table 8. As will be clear from the table, it was found that the test specimen 4-2 (55×55 mm; thickness=about 5 mm) prepared from the PVC molded product containing 7% of the antibacterial agent prepared in Example 2 formed an inhibition zone against *Escherichia coli*, and it was observed that the test specimen 4-1 prepared from the PVC molded product containing 14% of the antibacterial agent prepared in Example 2 formed an inhibition zone against Staphylococcus aureus. In the case of the test specimen 4-BL (50×50 mm; thickness=5 mm) for a blank test which contained no antibacterial agent, no inhibition zone was formed against the above-described two kinds of bacteria.

TABLE 8

| | Test as to formation of inhibition zone (Example 4) | | |
|---|---|---|---|
| Number of test specimen | *AMAS content (persentage) in PVC molded product | Test bacteria and fungi | Formation of inhibition zone |
| 4-1 | 14 | *Staphylococcus aureus* | formed |
| 4-BL | — | *Staphylococcus aureus* | not formed |
| 4-2 | 7 | *Escherichia coli* | formed |
| 4-BL | — | " | not formed |
| 4-3 | 10 | *Aspergillus flavus* | formed |
| 4-BL | — | " | not formed |

TABLE 8-continued

Test as to formation of inhibition zone (Example 4)

| Number of test specimen | *AMAS content (persentage) in PVC molded product | Test bacteria and fungi | Formation of inhibition zone |
|---|---|---|---|
| 4-4 | 15 | Aspergillus niger | formed |
| 4-BL | — | " | not formed |

PVC molded product: PVC-DOP-stabilizer
Specimen: 55 × 55 mm; thickness = about 5 mm
*Bactericidal AMAS prepared in Example 2

Next, as an antifungal power test, a test to establish whether or not an inhibition zone was formed against *Aspergillus flavus* and *Aspergillus niger* was carried out using test specimens 4-3 and 4-4 (50×50 mm; thickness=5 mm) prepared form the PVC molded products containing 10% and 15%, respectively, of the antibacterial agent prepared in Example 2. It was confirmed that an inhibition zone was formed in both cases. In the case of the test specimen 4-BL (50×50 mm; thickness=5 mm) for a blank test, no inhibition zone was formed against the above-described two kinds of fungi. The results of the tests as to the formation of an inhibition zone against the two kinds of bacteria and the two kinds of fungi clearly show that the PVC polymer containing AMAS according to the present invention has an antibacterial effect.

EXAMPLE 5

This example relates to the production of an AMAS having a bactericidal action and the trial production of an acrylic resin (AR) molded product containing this AMAS.

Two liters of a 0.1M $AgNO_3$—0.55M $Zn(NO_3)$, mixed solution was added to a dried AMAS powder ($1.3Na_2O.Al_2O_3.5.9SiO_2$; average particle diameter=0.4 μm). The resultant mixture was maintained for 4 hours under stirring at 20° to 25° C. to cause an ion exchange reaction. After the completion of the reaction, the reaction product was filtered and then rinsed to remove excessive silver and zinc ions from the solid phase. The rinsed product was dried at 100° to 110° C. and then pulverized into a fine powder using a pulverizer. By the above-described ion exchange reaction, it was possible to obtain 918 kg of bactericidal dried AMAS powder [Ag=2.57%; Zn=2.05% (on an anhydrous basis); molar ratio of $SiO_2/Al_2O_3$=5.9; average particle diameter Dav=0.9 μm; specific surface area SSA=81 $m^2/g$].

The bactericidal AMAS prepared bY the above-described process was heated to about 330° C. to remove water therefrom until the water content reached 2% or less. The dried product and AR (Shofu Bioresin: an acrylic resin used for false teeth) were mixed together in a predetermined weight ratio using an automatic mortar to prepare mixtures having various compositions. A small amount of a methacrylate ester for heat polymerization was added to and mixed with each of the mixtures under stirring. The resultant mixture was put in a mold and allowed to stand for about 12 hours. Next, the mixture was maintained for about 1 hour at 100° to 110° C. and then cooled. Thereafter, a molded product (100×100 mm; thickness=about 1.5 mm) was removed from the mold. The molded product was cut to prepare small test specimens (50×50 mm; thickness=1.5 mm) with which measurement of the change with time in the number of individuals of fungi was carried out as an antibacterial power evaluation test by the following method. Some of the results of the measurement are shown in Table 9.

TABLE 9

Change with time in number of individuals of inoculated fungus (Example 5)
unit: Number of individuals surviving in 1 ml of test solution

| Number of test specimen | Test fungus | Shaking time (hr) | | |
|---|---|---|---|---|
| | | 0 | 24 | 48 |
| 5-6 | Aspergillus niger | $2.3 \times 10^4$ | 0 | 0 |
| 5-10 | Aspergillus niger | $2.6 \times 10^4$ | $1.5 \times 10^4$ | $4.9 \times 10^3$ |
| 5-BL (blank test) | Aspergillus niger | $2.7 \times 10^4$ | $2.6 \times 10^4$ | $3.5 \times 10^4$ |

As will be clear from Table 9, it has been confirmed that, in the case of the test specimen 5-6 containing 11% of the dried bactericidal AMAS powder produced in this example, the number of individuals of a fungus (Aspergillus niger) was 0, that is, the individuals of the fungus died out completely, after 24 hours had elapsed after the start of the reaction. In the case of the test specimen 5-10 containing 0.15% of said AMAS, the number of individuals of the fungus gradually decreased. In the case of the test specimen 5-BL (for a blank test) containing no antibacterial agent, however, no reduction in the number of individuals of the fungus was found. It is clear from the results of the above-described test that the AR molded product containing bactericidal AMAS according to the present invention has an antibacterial effect.

EXAMPLE 6

In this example, a Cu-Ag-AMAS [molar ratio of $SiO_2/Al_2O_3$=18.8; Ag=2.03%; Cu=1.92% (on an anhydrous basis)] was prepared by using an AMAS represented by the composition formula of $1.3Na_2O.Al_2O_3.18.8SiO_2$ as an AMAS having a relatively high molar ratio of $SiO_2/Al_2O_3$ and substituting some of the Na exchange groups with silver and copper ions by the application of the same ion exchange method as the above. The prepared AMAS was then coated with a silicone coating agent, and this coated AMAS was used to coat paper to obtain antibacterial coated paper. More specifically, the bactericidal AMAS was heated at 300° C. under a vacuum to reduce the water content to 1% or less and then pulverized to obtain an activated fine powder (average particle diameter=2.8 μm; specific surface area SSA=34 $m^2/g$). Then, the activated fine powder was treated with a solution of a silicone coating agent [KF-96 (500 CPS) manufactured by Shin-ethu Chemical Industry Co., Ltd.] diluted with carbon tetrachloride, and the solid phase was separated thereafter. Then, the solid phase AMAS powder coated with the silicone film was heated under a vacuum to completely remove $CCl_4$ from the solid phase, thus eventually obtaining an AMAS having 2.5% of silicone coating. The resultant AMAS was wet-mixed with MC (methyl cellulose 8000 CPS) using water to prepare an MC—bactericidal AMAS (coated)—$H_2O$ slurry (0.15% of MC; 3.5% of Cu-Ag-AMAS). A test piece (100×100 mm, thickness=0.36 mm) of pilopack (white) was spray-coated with this slurry to produce antibacterial coated paper on a trial basis. As the above-described pilopack (white), Pilowhite (trade name; manufactured by Marusan Seishi Kabushiki Kaisha) was used. This is package cushioning paper one side of which is protuberant and which is produced by employing bleached wood pulp and using special paper-making and drying machines.

The antibacterial coated paper obtained in this example was cut to prepare a small test specimen (50×50 mm), and the change with time in the number of individuals of *Escherichia coli* was measured using the prepared test specimen. The result of the measurement are shown in Table 10. From the comparison between the test specimen 6-4 of the antibacterial paper [Cu=0.028%; Ag=0.030% (on a dry basis)] produced in this example on a trial basis and the test specimen [pilopack (white) 50×50 mm] containing no antibacterial agent, it is clear that the antibacterial coated paper produced in accordance with the present invention has an antibacterial effect. In this example, as described above, an AMAS of the present invention having 2.5% of silicone coating was employed as an antibacterial agent, and the AMAS was first formed into a slurry, together with MC, and then spray-coated on the surface of paper to obtain antibacterial coated paper. It has been confirmed that the formation of a thin film of silicone coating on the antibacterial agent of the present invention is effective in inactivating the reaction of the AMAS with the components of the paper or an additive, sizing agent or the like contained therein and also effective in preventing a change in color and fading of the paper.

TABLE 10

Change with time in number of individuals of inoculated bacteria (Example 6)
unit: Number of individuals surviving in 1 ml of test solution

| Number of test specimen | Test bacteria | Shaking time (hr) | | |
|---|---|---|---|---|
| | | 0 | 12 | 24 |
| 6-4 | *Escherichia coli* | 2.3 × 10$^4$ | 0 | 0 |
| 6-BL (blank test) | *Escherichia coli* | 2.1 × 10$^4$ | 2.3 × 10$^4$ | 3.5 × 10$^4$ |

EXAMPLE 7

This example relates to the production of paper mixed with an antibacterial AMAS specified in the present invention. The antibacterial paper in this example was produced under the following conditions. Ninety-three parts of purified bleached kraft wood pulp and 7 parts of the AMAS [Ag=2.70%; Cu=3.86% (on an anhydrous basis); molar ratio of $SiO_2/Al_2O_3$=6.4; average particle diameter Dav=0.15 μm, specific surface area SSA=116 m$^2$/g] produced in Example 2 on a trial basis were cast in a macerating machine to effect maceration under stirring for 7 minutes. This raw material was then transferred to a beater to effect beating for about 13 minutes to that LSR was 40°. The beaten raw material was mixed with as solid constituents 0.5% by weight of a commercially available rosin sizing agent, 2.0% by weight of a commercially available aluminum sulfate, and 3.0% by weight of a heavy-duty cationic synthetic resin [Yuramin P-5500 (trade name; manufactured by Mitsui Toatsu kagaku)] to prepare a paper-making material. A sheet of wet paper having a thickness of about 0.4 mm and a dry weight of 205 g/m, was made using the prepared paper-making material and employing a hand paper-making apparatus. The wet paper was dried for 10 minutes using a rotary drier having the surface temperature adjusted to 105° C. to make paper mixed with bactericidal AMAS on a trial basis.

The antibacterial paper made by the above-described method was cut to prepare a test specimen (about 50×50 mm), and measurement of the death rate with respect to *Staphylococcus aureus* was carried using this test specimen and in accordance with the aforementioned method. The death rate measured after 24 hours had elapsed after the start of the reaction carried out at 37° C. was 100%. Thus, it has been confirmed that the paper containing AMAS according to the present invention has a strong bactericidal action.

EXAMPLE 8

Figure 7A:
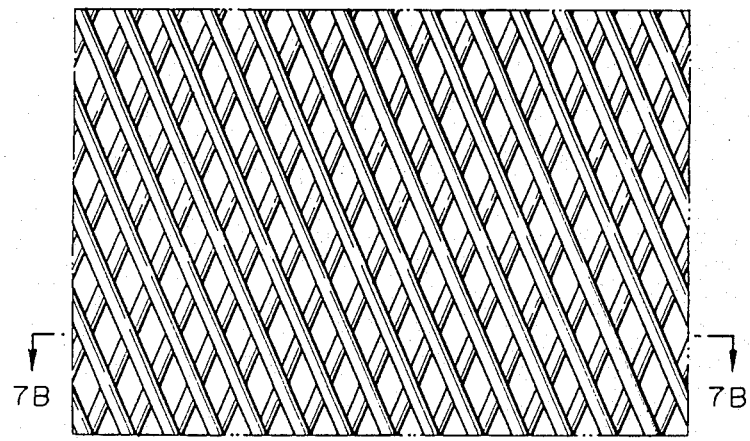
FIG. 7 shows the configuration of an LDPE foam net containing AMAS having a bactericidal action according to the present invention experimentally produced in Example 8.
Figure 7B:
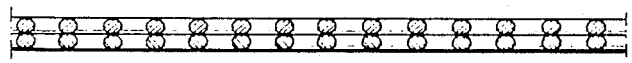
Figure 8:
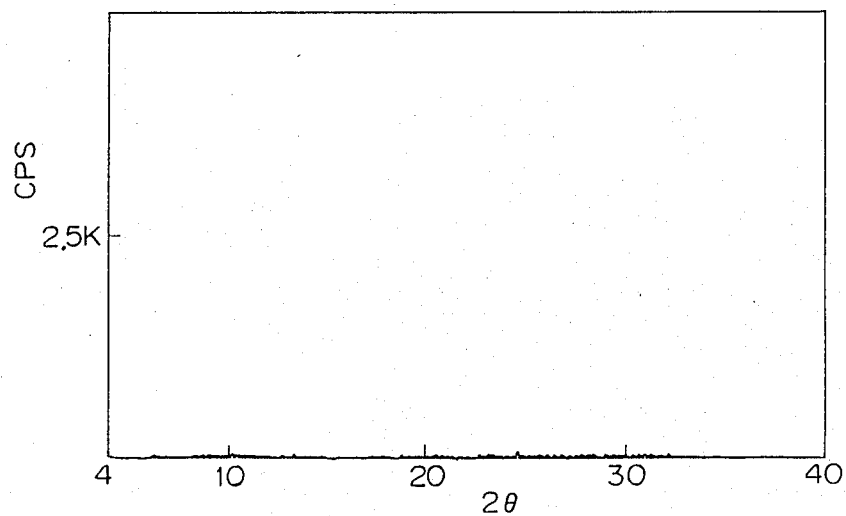
FIGS. 8 and 9 respectively show X-ray diffraction patterns of amorphous aluminosilicates partially converted into calcium and potassium, in which 5-B in FIG. 9 represents the diffraction pattern of a sample having a higher potassium content in AMAS than that of 5-A.
Figure 9:
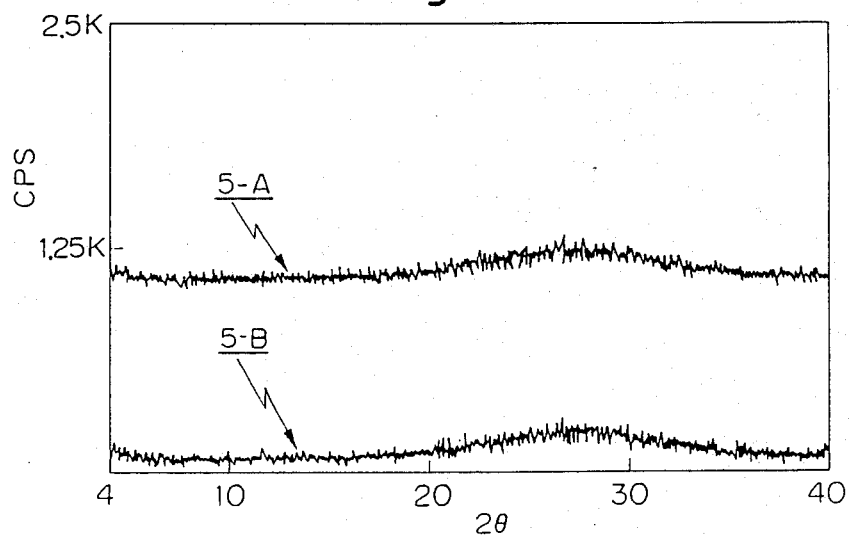

This example relates to the trial production of a polyethylene (PE) foam in the shape of a net having an antibacterial function according to the present invention and the antibacterial power test carried out thereon. The bactericidal AMAS [Ag=3.01%; Cu=4.84% (on an anhydrous basis); average particle diameter Dav=0.32 μm; specific surface area SSA=43 m$^2$/g] prepared in Example 1 and LDPE (MI35; density=0.919) were compounded together in a predetermined weight ratio, and the mixture was put in an extrusion foaming machine. With the temperature maintained at about 220° C., the mixture was melted and mixed, and butane was introduced therein as a foaming agent. While doing so, the mixture was extruded from the nozzle. Thus, a net-shaped LDPE foam containing 2% of the bactericidal AMAS such as that shown in FIG. 7 was produced on a trial basis. The antibacterial net produced in this example was cut to prepare a test specimen (about 80×60 mm), and the change with time in the number of individuals of *Staphylococcus aureus* was measured using the prepared test specimen and in accordance with the aforementioned method. The results of the measurement are shown in Table 11. The number 8-BL in Table 11 represents a test specimen (mixed with no antibacterial agent) having the same configuration as that of the test specimen 8-1. From the comparison between the values shown in Table 11, it is clear that the antibacterial net according to the present invention has an excellent antibacterial effect.

TABLE 11

Change with time in number of individuals of bacteria (Example 6)
unit: Number of individuals surviving in 1 ml of test solution

| Number of test specimen | Test bacteria | Shaking time (hr) | |
|---|---|---|---|
| | | 0 | 24 |
| 8-1 | *Staphylococcus aureus* | 3.8 × 10$^4$ | 0 |
| 8-BL | " | 3.6 × 10$^4$ | 5.9 × 10$^3$ |

EXAMPLE 9

This examples relates to the trial production of HDPE (high-density polyethylene) monofilament. As a HDPE, Showrex F5012M (MI=1.2) was employed, and as an inorganic antibacterial agent, an antibacterial AMAS activated powder . [Ag=3.01%; Cu=4.84% (on an anhydrous basis); average particle diameter Dav=0.32 μm; specific surface area SSA=43 m$^2$/g] which was the same as that used in Example 1 was employed. In the mixtures of the two materials, the latter was maintained in the proportion of 2.5% (9-1) and 3% (9-2). HDPE monofilaments having a bactericidal action were produced on a trial basis by an extrusion process (the extrusion conditions temperature=230° C.±10° C.; pressure=100 to 110 kg/cm,; retention time=10 to 15 minutes; duty=1.5 kg/hr; screw speed=20 rpm; ratio of length (L) to diameter (D) of screw of extrusion machine L/D=25). Then, each monofilament was oriented about 9 times to prepare a monofilament of about 410 denier.

The eventually oriented monofilaments had satisfactory strength and physical properties. With these monofilaments employed, measurement of the death rate was carried out as an antibacterial power test using two bacteria, i.e., *Escherichia coli* and *Staphylococcus aureus*, and in accordance with the aforementioned method.

1% of the above-described inorganic antibacterial agent, the number of individuals surviving of *Escherichia coli* measured after 24 hours reached 0 as shown in Table 13. It is clear from the comparison between the test specimens 10-1 and 10-2 (for a blank test; mixed with no antibacterial agent) that the inorganic antibacterial agent according to the present invention has a bactericidal effect. Next, the change with time in the number of individuals of *Staphylococcus aureus* was measured. It is clear from the comparison with a blank test (test specimen 10-4; mixed with no antibacterial agent) that the PP film (test specimen 10-3) containing 2% of the above-described inorganic antibacterial agent has a bactericidal effect.

TABLE 13

| Change with time in number of individuals of inoculated bacteria (Example 10) unit: Number of individuals surviving in 1 ml of test solution | | | | | |
|---|---|---|---|---|---|
| Number of test specimen | Test bacteria | Shaking time (hr) | | | |
| | | 0 | 5 | 24 | 48 |
| 10-1 | *Escherichia coli* | $1.5 \times 10^4$ | $2.3 \times 10^2$ | 0 | 0 |
| 10-2 (for blank test) | " | $1.9 \times 10^4$ | $5.9 \times 10^3$ | — | $1.4 \times 10^4$ |
| 10-3 | *Staphylococcus aureus* | $1.5 \times 10^4$ | $2.2 \times 10^3$ | $5.3 \times 10^1$ | 0 |
| 10-4 (for blank test) | " | $1.8 \times 10^4$ | $3.3 \times 10^3$ | $4.9 \times 10^2$ | $5.1 \times 10^2$ |

The results of the test are shown in Table 12. As will be clear from Table 12, it has been confirmed that the HDPE monofilaments (9-1 and 9-2) produced in this example on a trial basis exhibit satisfactory antibacterial power.

TABLE 12

| Measurement of death rate (Example 9) | | | |
|---|---|---|---|
| Number of test specimen | Antibacterial metal content (%) in filament | Death rate (%) | |
| | | *Escherichia coli* | *Staphylococcus aureus* |
| 9-1 | Ag = 0.076; Cu = 0.118 | 100 | 98 |
| 9-2 | Ag = 0.089; Cu = 0.142 | 100 | 100 |

EXAMPLE 10

This example relates to the trial production of PP (polypropylene) film containing AMAS having a bactericidal action. In this example, a PP material (A 4141; manufactured by Chisso Corporation) was mixed with an activated powder (average particle diameter Dav=1.1 μm; H₂O=1.3%) of a composite AMAS (Ag=2.59%; Zn=0.68%; Cu=1.94% (on an anhydrous basis); molar ratio of $SiO_2/Al_2O_3$=5.9; specific surface area SSA=83 m²/g) obtained by substituting with $Ag^+$, $Zn^{2+}$ and $Cu^{2+}$ some of $Na^+$ of amorphous sodium aluminosilicate of the same kind of material as that employed in Example 5 to prepare mixtures having AMAS contents of 1% and 2%, respectively. Then, films having a thickness of about 50 μm were produced on a trial basis by the inflation method with the cylinder temperature maintained at 190° to 220° C., the die opening temperature at about 220° C., and the screw speed at 20 rpm. Each film was cut to prepare a test specimen (100×100 mm), and measurement of the change with time in the number of individuals of each of inoculated bacteria was carried out using the prepared test specimen and in accordance with the aforementioned method. The result of the test are shown in Table 13. In the case of the PP film (test specimen 10-1) containing

EXAMPLE 11

To a polyethylene terephthalate chip having a limiting viscosity number of 0.660 measured with a phenol ethane tetrachloride equivalent weight mixed solution at 20° C., the bactericidal AMAS activated powder employed in Example 1 was added in amounts of 1% and 1.5% by weight, and each of the mixtures was melt-spun from a spinning nozzle having 400 bores under the conditions: spinning temperature=285° C.; delivery rate=300 g/mm; and spinning rate=550 m/mm. The resultant un-oriented sub-tows were converged to form an unoriented fiber tow of about 2 million denier. This tow was oriented 4.1 times at 80° C. and then crimped. Thereafter, the oriented tow was cut to prepare a staple fiber. The antibacterial effects of the resultant staple fibers are shown in Table 14.

TABLE 14

| Experiment number | Amount of AMAS | Antibacterial effect* (death rate) |
|---|---|---|
| 1 | 1 wt. % | 98.1% |
| 2 | 1.5 wt. % | 99.4% |

*Antibacterial effect test was carried out using cultured coliform bacillus in accordance with "Method of testing growth inhibition against bactera of fibrous product subjected to antibacterial deodorization" examined at the fibrous product sanitary processing conference.

EXAMPLE 12

To a 6-nylon dried chip having a relative viscosity (η rel) of 2.3 measured with a 95% sulfuric acid, the bactericidal AMAS activated powder employed in Example 1 was added so as to prepare two mixtures containing 1% and 3% by weight of the AMAS. The mixtures were melt-spun and then oriented by conventional methods to obtain two kinds of oriented yarn of 120 denier and consisting of 4 filaments. The antibacterial effects of the oriented yarns were measured in accordance by the evaluation method employed in Example 11. The results of the test are shown in Table 15

TABLE 15

| Experiment number | Amount of AMAS | Antibacterial effect (death rate) |
|---|---|---|
| 1 | 1 wt. % | 98.0% |
| 2 | 3 wt. % | 99.5% |

The polymer containing AMAS according to the present invention has a remarkable bactericidal effect against general bacteria and fungi as described above. The use of the present invention not only enables the polymer itself to be made antibacterial but also permits sterilization of the atmosphere which is in contact with the polymer. Since the bactericidal AMAS according to the present invention is uniformly dispersed in and held on the polymer considerably stably, the amount of metal which elutes or separates from the polymer is very small. Accordingly, the safety level is considerably high, advantageously.

A test specimen 3-5 [25×10 mm; thickness=2 mm; Ag=0.26%; Cu=0.38%; trace components of 1% or less (Zn, Ba and Ca)] was prepared from a PVC molded product having the same chemical composition as that of the test specimen 3-1 exemplarily shown in Example 3, and city water (Ca=3.7 ppm; Mg=2.1 ppm; Cl=4 ppm; pH=5.01) was added to the test specimen 3-5 so that the ratio of the test specimen to the city water was 1 g/l. The liquid was stirred occasionally and sampled every time a predetermined period had elapsed to measure the Cu and Ag concentrations and pH as shown in Table 16 (test at room temperature).

TABLE 16

Eluation of antibacterial metal from PVC sheet

| Number of test specimen | Eluated metal (PPb) & pH | Time elapsed (hr) | | | | |
|---|---|---|---|---|---|---|
| | | 10 | 50 | 100 | 500 | 1000 |
| 3-5 | Cu | 2 | 7 | 17 | 22 | 38 |
| | Ag | 0.6 | 0.8 | 1 | 3 | 9 |
| | pH | 7.03 | 7.03 | 7.02 | 7.03 | 7.04 |

As will be clear from Table 16, copper and silver, which are antibacterial metals, eluated extremely slightly, and the amounts of these metals which had eluated after 1000 hours had elapsed after the start of the test carried out at room temperature were only 38 and 9 PPb, respectively. This also confirms that the safety level of the polymer of the present invention is considerably high. As an example of eluation of antibacterial metals from a polymer, eluation of metals from a PP molded product is shown in Table 17. City water (Ca=4.6 ppm; Mg=3.2 ppm; Cl=4 ppm; pH=7.03) was added to a PP molded product 2-5 (25×25 mm; thickness=1.5 mm) containing a bactericidal AMAS having the same composition as that of the test specimen 2-2 in Example 2 so that the ratio of the test specimen to the city water was 1 g/l. The liquid was stirred occasionally and sampled every time a predetermined period had elapsed to measure the Cu and Ag concentrations and pH in the aqueous solution phase as shown in Table 17 (test at room temperature). As will be clear from Table 17, the amounts of antibacterial metals which eluated from the polymer in this example were very small, i.e., Ag=10 PPb and Cu=21 PPb, even after 500 hours. This confirms that the polymer containing AMAS according to the present invention has a considerably high safety level.

TABLE 17

Eluation of antibacterial metal from PP molded product

| Number of test specimen | Eluated metal (PPb) & pH | Time elapsed (hr) | | | |
|---|---|---|---|---|---|
| | | 10 | 50 | 100 | 500 |
| 2-5 | Ag | 0.5 | 1 | 3 | 10 |
| | Cu | 3 | 5 | 7 | 21 |
| | pH | 7.08 | 7.08 | 7.09 | 7.08 |

What is claimed is:

1. A polymer containing amorphous aluminosilicate particles, said polymer comprising an organic polymer and amorphous aluminosilicate solid particles coating agent, at least some of said amorphous aluminosilicate solid particles having antibacterial or bactericidal metal ions on ion-exchangeable sites existing on and within the particles, wherein said amorphous aluminosilicate solid particles have a specific surface area of at least 5 $m^2/g$ and a $SiO_2/Al_2O_3$ molar ratio of at least 1.3.

2. A polymer according to claim 1, wherein said aluminosilicate solid particles having bactericidal metal ions are produced by partial or complete ion-exchange of exchangeable M' ions in an amorphous, aluminosilicate having the formula $xM'_2O.Al_2O_3.ySiO_2$, here M' is monovalent or divalent metal ion without antibacterial or bactericidal action and said bactericidal metal ion is selected from the group consisting of Ag, Cu, Zn, Hg, Sn, Pb, Bi, Cd, Cr and mixtures thereof, x is a number between 0.6 and 1.8 inclusive, y is a number between 1.3 and 30 inclusive and n is the valence of M'.

3. A polymer according to claim 1, wherein said amorphous aluminosilicate solid particles have an average particle diameter of 20 microns or less.

4. A polymer according to claim 1, wherein said antibacterial or bactericidal metal ions are one or more metal ions selected from the group consisting of silver, copper, zinc, mercury, tin, lead, bismuth, cadmium and chromium.

5. A polymer according to claim 1 wherein said amorphous aluminosilicate solid particles are between 0.005 and 50% by weight inclusive of the weight of the total polymer, based on the anhydrous weight of said aluminosilicate.

6. A polymer containing amorphous aluminosilicate particles, said polymer comprising an organic polymer and amorphous aluminosilicate solid particles, at least some of said amorphous aluminosilicate solid particles having antibacterial or bactericidal metal ions on ion-exchangeable sites existing on and within the particles, wherein said amorphous aluminosilicate solid particles in an uncoated form have a specific surface area of at least 5 $m^2/g$ and a $SiO_2/Al_2O_3$ molar ratio of at least 1.3, said amorphous aluminosilicate solid particles being coated with a silicone resin coating agent or a fluorine resin coating agent.

7. A polymer according to claim 6, wherein the coating agent content in the amorphous aluminosilicate solid is at least 0.01%.

8. A process for producing a polymer containing coated amorphous aluminosilicate particles with antibacterial or bactericidal metal ions comprising:
coating amorphous aluminosilicate solid particles by applying thereto a silicone resin coating agent, fluorine resin coating agent or a solution of either one of said two coating agents diluted with a solvent;
wherein said antibacterial or bactericidal metal ions are one or more metal ions selected from the group consisting of silver, copper, zinc, mercury, tin, lead, bismuth, cadmium and chromium, and said amorphous aluminosilicate solid particles have an average particle diameter of 20 microns or less, a specific surface area of at least 5 $m^2/g$, and a $SiO_2/Al_2O_3$ molar ratio of at least 1.3.

* * * * *

UNITED STATES PATENT AND TRADEMARK OFFICE
CERTIFICATE OF CORRECTION

PATENT NO. : 4,959,268
DATED : September 18, 1990
INVENTOR(S) : HAGIWARA et al.

It is certified that error appears in the above-identified patent and that said Letters Patent is hereby corrected as shown below:

| | |
|---|---|
| Column 36, lines 12 & 13 | Delete "coating agent" |
| Column 36, line 21 | After "M'", insert -- metal -- |
| Column 36, line 22 | Delete "$xM'_2O.Al_2O_3.ySiO_2$,", insert therefor -- $xM'_{\frac{2}{n}}O.Al_2O_3.ySiO_2$ -- |
| Column 36, line 22 | Delete "here", insert therefor -- where -- |
| Column 36, line 53 | After "solid", insert -- particles -- |

Signed and Sealed this

Seventh Day of September, 1993

Attest:

BRUCE LEHMAN

*Attesting Officer*     Commissioner of Patents and Trademarks